United States Patent [19]

Hamatani et al.

[11] Patent Number: 5,436,224
[45] Date of Patent: Jul. 25, 1995

[54] 1,3-OXAZIN-4-ONE DERIVATIVES, HERBICIDES CONTAINING THE SAME, AND NOVEL INTERMEDIATES FOR PREPARING THE SAME

[75] Inventors: Takeshi Hamatani, Tsukuba; Hirokazu Hasebe, Himeji; Keiichi Hayashizaki, Ami; Yoshihiro Usui, Ami; Chiharu Yasumoto, Ami; Atsushi Go, Ami; Mitsuru Hikido, Ami; Kumiko Tamura, Ami; Kazuo Jikihara, Ami, all of Japan

[73] Assignees: Mitsubishi Petrochemical Co., Ltd., Tokyo; Daicel Chemical Industries, Ltd., Osaka, both of Japan

[21] Appl. No.: 122,563

[22] PCT Filed: Jan. 28, 1993

[86] PCT No.: PCT/JP93/00105
§ 371 Date: Sep. 30, 1993
§ 102(e) Date: Sep. 30, 1993

[87] PCT Pub. No.: WO93/15064
PCT Pub. Date: Aug. 5, 1993

[30] Foreign Application Priority Data

Jan. 30, 1992 [JP] Japan ............ 4-040108

[51] Int. Cl.$^6$ ............ A01N 43/86; C07D 265/06
[52] U.S. Cl. ............ 504/223; 544/97; 514/228.8
[58] Field of Search ............ 544/97; 514/228.8; 504/223

[56] References Cited

U.S. PATENT DOCUMENTS

| 2,582,128 | 1/1952 | Hurwitz | 260/566 |
| 5,006,157 | 4/1991 | Ohba et al. | 71/95 |
| 5,076,834 | 12/1991 | Ohba et al. | 71/94 |

FOREIGN PATENT DOCUMENTS

| 59-172482 | 9/1984 | Japan . |
| 2-178274 | 7/1990 | Japan . |
| 4-89485 | 3/1992 | Japan . |

OTHER PUBLICATIONS

CA 119:219601, Osabe et al., (1993).
CA 117:90305, Goto et al., (1992).
Maujean et al., Tetrahedron Letters, No. 33, pp. 2905–2908 (1976).
Sato et al., Heterocycles, vol. 17, (1982), pp. 297–300.
Yamamoto et al., Chem. Pharm. Bull., vol. 35(5) pp. 1860–1879 (1987).
Sato et al., Chem. Pharm. Bull., vol. 31(6) pp. 1896–1909 (1983).
Sato et al., Chem. Pharm. Bull., vol. 32(7) pp. 2602–2608 (1984).

*Primary Examiner*—Mukund J. Shah
*Assistant Examiner*—Matthew V. Grumbling
*Attorney, Agent, or Firm*—Wenderoth, Lind & Ponack

[57] ABSTRACT

1,3-Oxazin-4-one derivatives represented by general formula (I)

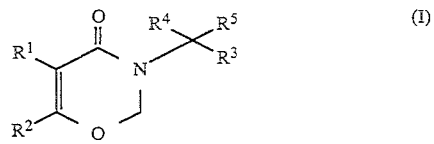

wherein $R^1$ is a lower alkyl group, a lower alkenyl group, an aryl group which may be substituted, or an aralkyl group which may be substituted;

$R^2$ is a hydrogen atom or a lower alkyl group;

$R^3$ is a lower alkyl group, an aryl group which may be substituted, or an aralkyl group which may be substituted; and $R^4$ and $R^5$, independently, each is a lower alkyl group, or $R^4$ and $R^5$, taken together with the carbon atom to which they are bonded, combine to form a 3- to 8-membered carbocyclic group which may have a branch of a lower alkyl group. These compounds have broad herbicidal spectra and potent herbicidal activities and in addition high safety to useful crops, so that they are useful as herbicides.

8 Claims, No Drawings

1,3-OXAZIN-4-ONE DERIVATIVES, HERBICIDES CONTAINING THE SAME, AND NOVEL INTERMEDIATES FOR PREPARING THE SAME

This is a national stage application (37 CFR 1.371) of PCT/JP93/00105, filed Jan. 28, 1993.

TECHNICAL FIELD

This invention relates to novel 1,3-oxazin-4-one derivatives having a tertiary alkyl substituent at the 3-position thereof, method for preparing the same, use thereof as a herbicide, and novel intermediates for preparing the same.

BACKGROUND ART

Certain types of 4H-2,3-dihydro-1,3-oxazin-4-one derivatives are described in, for example, Tetrahedron Lett., (33), 2905 (1976), Heterocycles, 17, 298 (1982), Chem. Pharm. Bull., 35(5), 1871 (1987), etc. and thus they are known.

However, the compounds described in the above-mentioned publications differ from the compounds of this invention since none of them has a tertiary alkyl substituent on the 3-position of a 1,3-oxazine ring and no mention is made of their herbicidal activity and plant growth control activity.

U.S. Pat. Nos. 5,006,157 and 5,076,834 disclose 1-(1-methyl-1-phenylethyl)-3-phenyl-1,2,5,6-tetrahydropyridin-2-one derivatives and their use as a herbicide.

DISCLOSURE OF INVENTION

According to this invention, there are provided 1,3-oxazin-4-one derivatives represented by general formula (I) which follows

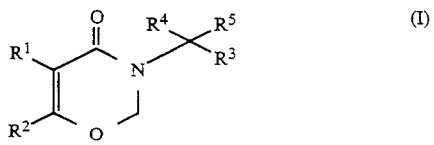

wherein $R^1$ is a lower alkyl group, a lower alkenyl group, an aryl group which may be substituted, or an aralkyl group which may be substituted;

$R^2$ is a hydrogen atom or a lower alkyl group;

$R^3$ is a lower alkyl group, an aryl group which may be substituted, or an aralkyl group which may be substituted; and $R^4$ and $R^5$, independently each is a lower alkyl group, or $R^4$ and $R^5$, taken together with the carbon atom to which they are bonded, combine to form a 3- to 8-membered carbocyclic group which may have, as a substituent, a lower alkyl group.

The compounds of general formula (I) above provided by this invention have remarkable selective herbicidal activity, give no phytotoxicity to useful crops, and exhibit excellent herbicidal activity to various weeds at a very low dose, and therefore they are useful as herbicides.

BEST MODE FOR CARRYING OUT THE INVENTION

In the description and claims, the term "lower" means that groups or compounds to which this term is attached have 6 or less carbon atoms, preferably 4 or less carbon atoms.

"Lower alkyl group" may be either straight chained or branched chained, and includes, for example, methyl, ethyl, n-propyl, isopropyl, n-butyl, isobutyl, sec-butyl, tert-butyl, n-pentyl, isopentyl, neopentyl, tert-pentyl, n-hexyl, etc. groups.

"Lower alkenyl group" may be either straight chained or branched chained, and includes, for example, allyl, 2-methyl-2-propenyl, 2-butenyl, 3-butenyl, 3-methyl-2-butenyl, etc., groups.

"Lower alkynyl group" may be either straight chained or branched chained, and includes, for example, 2-propynyl, 1-methyl-2-propynyl, 2-butynyl, 3-butynyl, etc., groups.

"Halogen atom" includes four species, i.e., fluorine atom, chlorine atom, bromine and iodine atom.

"Lower alkoxy group" means lower alkyl-O-group of which the lower alkyl moiety has the above-described meaning, and includes, for example, methoxy, ethoxy, n-propoxy, isopropoxy, n-butoxy, isobutoxy, sec-butoxy, tert-butoxy, n-pentoxy, etc., groups.

"Lower haloalkyl group" means one of which at least one hydrogen atom is substituted by a halogen atom, and includes, for example, trifluoromethoxy, difluoromethoxy, chlorodifluoromethoxy, 2-chloroethoxy, 1,1,2,2-tetrafluoroethoxy, 3-chloropropoxy, 2,2,3,3,3-pentafluoropropoxy, etc., groups.

"Aryl group" may be either monocyclic or polycyclic, and specific examples thereof include phenyl, naphthyl, etc., groups. Substituent group(s) on the ring of the "aryl group which may be substituted" may include halogen atoms, lower alkyl groups, lower alkoxy groups, lower haloalkyl groups, lower haloalkoxy groups, a nitro group, etc. The aryl group may be substituted with at least one, preferably 1 to 4, and more preferably 1 to 3, of the substituent groups. Specific examples of such a substituted group include 2-fluorophenyl, 4-chloro-2-naphthyl, 2-tolyl, 3-tolyl, 3,5-dichloro-4-methylphenyl, 3,5-diisopropylphenyl, 3,5-dichlorophenyl, 3,5-dimethoxyphenyl, 3,5-bis(difluoromethoxy)phenyl, 3-nitrophenyl, 3-(trifluoromethyl)phenyl, 3-(2chloroethyl)phenyl, 3,5-bis(3-bromopropyl)phenyl, 3,5-bis(1,1-dimethylethyl)phenyl, 3,5-diethylphenyl, 3,5dibromophenyl, 3,5-diiodophenyl, 3,4,5-tribromophenyl, 3-chloro-2-fluorophenyl, 3,5-dichloro-2-fluorophenyl, 2,6-difluorophenyl-3-chlorophenyl, 2,6-difluoro-3,5-dichlorophenyl, 2,3,5-trifluorophenyl, 3-fluoro-4-methylphenyl, 3,5-difluoro-4-methylphenyl, 3,5-difluoro-4-methoxyphenyl, 4-methyl-3,5-bis(trifluoromethyl)phenyl, 4-methoxy-3-(trifluoromethyl)phenyl, etc., groups.

"Aralkyl group" means a lower alkyl group substituted with an aryl group of whose aryl and lower alkyl moieties have the same meanings as defined above, respectively, and include, for example, benzyl, phenethyl, 3-phenylpropyl, 4-phenylbutyl, etc. , groups. "Aralkyl group which may be substituted" means an aryl-substituted lower alkyl group whose aryl moiety is an "aryl group which may be substituted" as described above, and includes, for example, (2-chlorophenyl)methyl, 1-(3-chlorophenyl)ethyl, 1-methyl-1-phenylethyl, 1-methyl-2-phenylethyl, 1-ethyl-2-(3-trifluoromethylphenyl)ethyl, (2-difluoromethoxyphenyl)methyl, etc., groups.

"3- to 8-Membered carbocyclic group which may have, as a substituent a lower alkyl group" includes cycloalkyl groups which may be substituted with one or more lower alkyl groups, for example, cyclopropyl, cyclobutyl, cyclopentyl, cyclohexyl, cycloheptyl, cyclooctyl, 2,2-dimethylcyclopropyl, 3,5-diethylcyclohexyl, etc., groups.

Among the compounds represented by formula (I) described above, preferred groups of compounds include those compounds of formula (I) in which $R^1$ is a branched chain lower alkyl group (for example, isopropyl, isobutyl, etc., groups), or a phenyl group which may be substituted with one substituent selected from the group consisting of a halogen atom and a lower alkyl group;

$R^2$ is a methyl group or an ethyl group;

$R^3$ is an aryl group which may be substituted with 1 to 3 substituents selected from the group consisting of a halogen atom, a lower alkyl group, a lower haloalkyl group and a lower haloalkoxy group; and $R^4$ and $R^5$ each is a methyl group.

More preferred compounds of formula (I) are compounds of formula (I-1) below

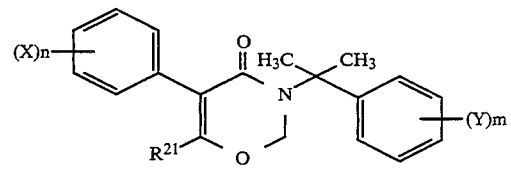

wherein $R^{21}$ is a methyl group or an ethyl group;

X is a halogen atom or a lower alkyl group;

Y is a halogen atom, a lower haloalkyl group or a lower haloalkoxy group;

m is 0, 1, 2 or 3; and n is 0 or 1.

Specific examples of the compounds of formula (I) above provided by this invention are shown in Tables 1 to 5 hereinbelow. In the tables, abbreviations used have the following meanings.

Me: methyl group;
Et: ethyl group;
Pr: propyl group
iPr: isopropyl group;
Bu: n-butyl group;
iBu: isobutyl group;
sBu: s ec-butyl group;
tBu: tert-butyl group;
Hex: n-hexyl group;
Ph: phenyl group; and
-: no substituent.

TABLE 1

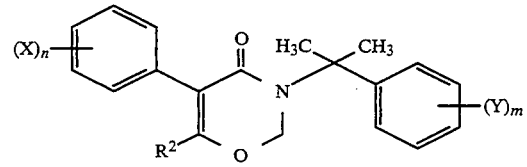

| Compound No. | (X) n | (Y) m | $R^2$ | Melting Point [°C.] |
|---|---|---|---|---|
| 1 | — | — | Me | 94.0–96.0 |
| 2 | 2-F | — | Me | 91.5–94.0 |
| 3 | 3-F | — | Me | 45.0–47.0 |
| 4 | 4-F | — | Me | Oily |
| 5 | 2-Cl | — | Me | 114.5–118.0 |
| 6 | 3-Cl | — | Me | Oily |
| 7 | 4-Cl | — | Me | 107.5–112.0 |
| 8 | 2-Br | — | Me | |
| 9 | 4-I | — | Me | |
| 10 | 2-F, 3-F | — | Me | |
| 11 | 2-F, 4-F | — | Me | |
| 12 | 2-F, 5-F | — | Me | |
| 13 | 2-F, 6-F | — | Me | |
| 14 | 3-F, 4-F | — | Me | |
| 15 | 3-F, 5-F | — | Me | |
| 16 | 2-F, 4-F, 6-F | — | Me | |
| 17 | 2-F, 3-F, 4-F, 5-F, 6-F | — | Me | |
| 18 | 2-Cl, 4-Cl | — | Me | |
| 19 | 3-Cl, 5-Cl | — | Me | |
| 20 | 2-Cl, 4-Cl, 6-Cl | — | Me | |
| 21 | 2-Cl, 3-Cl, 4-Cl, 5-Cl, 6-Cl | — | Me | |
| 22 | 2-Cl, 6-F | — | Me | |
| 23 | 2-Me | — | Me | 95.5–97.0 |
| 24 | 3-Me | — | Me | |
| 25 | 4-Me | — | Me | |
| 26 | 2-Me, 4-Me | — | Me | |
| 27 | 3-Me, 5-Me | — | Me | |
| 28 | 2-Me, 4-Me, 6-Me | — | Me | |
| 29 | 2-Et | — | Me | |
| 30 | 3-Et | — | Me | |
| 31 | 4-Et | — | Me | |
| 32 | 4-Pr | — | Me | |
| 33 | 2-iPr | — | Me | |
| 34 | 3-iPr | — | Me | |
| 35 | 4-iPr | — | Me | |
| 36 | 2-Bu | — | Me | |

TABLE 1-continued

| Compound No. | (X) n | (Y) m | R² | Melting Point [°C.] |
|---|---|---|---|---|
| 37 | 3-Bu | — | Me | |
| 38 | 4-Bu | — | Me | |
| 39 | 2-iBu | — | Me | |
| 40 | 3-sBu | — | Me | |
| 41 | 4-tBu | — | Me | |
| 42 | 2-Hex | — | Me | |
| 43 | 4-Hex | — | Me | |
| 44 | 2-Cl, 3-Me, 4-Cl | — | Me | |
| 45 | 2-OMe | — | Me | Oily |
| 46 | 3-OMe | — | Me | |
| 47 | 4-OMe | — | Me | |
| 48 | 2-OMe, 4-OMe | — | Me | |
| 49 | 2-OMe, 6-OMe | — | Me | |
| 50 | 3-OMe, 5-OMe | — | Me | |
| 51 | 3-OMe, 4-OMe, 5-OMe | — | Me | |
| 52 | 2-OEt | — | Me | |
| 53 | 4-OEt | — | Me | |
| 54 | 3-OPr | — | Me | |
| 55 | 3-OiPr | — | Me | |
| 56 | 2-OBu | — | Me | |
| 57 | 4-OBu | — | Me | |
| 58 | 2-OiBu | — | Me | |
| 59 | 2-OsBu | — | Me | |
| 60 | 4-OtBu | — | Me | |
| 61 | 4-OHex | — | Me | |
| 62 | 2-CF$_3$ | — | Me | 106.0–109.0 |
| 63 | 3-CF$_3$ | — | Me | Oily |
| 64 | 4-CF$_3$ | — | Me | |
| 65 | 3-CF$_3$, 5-CF$_3$ | — | Me | |
| 66 | 2-CH$_2$CF$_3$ | — | Me | |
| 67 | 2-CF$_2$CF$_3$ | — | Me | |
| 68 | 2-NO$_2$ | — | Me | |
| 69 | 3-NO$_2$ | — | Me | |
| 70 | 4-NO$_2$ | — | Me | |
| 71 | 2-NO$_2$, 4-NO$_2$ | — | Me | |
| 72 | 2-CF$_3$, 4-NO$_2$ | — | Me | |
| 73 | — | 3-Cl | Me | 66.5–68.5 |
| 74 | 2-F | 3-Cl | Me | 68.0–72.0 |
| 75 | 3-F | 3-Cl | Me | 58.5–62.0 |
| 76 | 4-F | 3-Cl | Me | Oily |
| 77 | 2-Cl | 3-Cl | Me | 123.5–126.0 |
| 78 | 3-Cl | 3-Cl | Me | Oily |
| 79 | 4-Cl | 3-Cl | Me | Oily |
| 80 | 2-Br | 3-Cl | Me | |
| 81 | 3-Br | 3-Cl | Me | |
| 82 | 4-Br | 3-Cl | Me | |
| 83 | 2-I | 3-Cl | Me | |
| 84 | 3-I | 3-Cl | Me | |
| 85 | 4-I | 3-Cl | Me | |
| 86 | 2-F, 3-F | 3-Cl | Me | |
| 87 | 2-F, 4-F | 3-Cl | Me | |
| 88 | 2-F, 5-F | 3-Cl | Me | |
| 89 | 2-F, 6-F | 3-Cl | Me | |
| 90 | 3-F, 4-F | 3-Cl | Me | |
| 91 | 3-F, 5-F | 3-Cl | Me | |
| 92 | 2-F, 4-F, 6-F | 3-Cl | Me | |
| 93 | 2-F, 3-F, 4-F, 5-F, 6-F | 3-Cl | Me | |
| 94 | 2-Cl, 3-Cl | 3-Cl | Me | |
| 95 | 2-Cl, 4-Cl | 3-Cl | Me | |
| 96 | 2-Cl, 5-Cl | 3-Cl | Me | |
| 97 | 2-Cl, 6-Cl | 3-Cl | Me | |
| 98 | 3-Cl, 4-Cl | 3-Cl | Me | |
| 99 | 3-Cl, 5-Cl | 3-Cl | Me | |
| 100 | 2-Cl, 4-Cl, 6-Cl | 3-Cl | Me | |
| 101 | 2-Cl, 3-Cl, 4-Cl, 5-Cl, 6-Cl | 3-Cl | Me | |
| 102 | 2-F, 3-Cl | 3-Cl | Me | |
| 103 | 2-Cl, 6-F | 3-Cl | Me | |
| 104 | 2-Me | 3-Cl | Me | 92.0–96.0 |
| 105 | 3-Me | 3-Cl | Me | |
| 106 | 4-Me | 3-Cl | Me | |

TABLE 1-continued

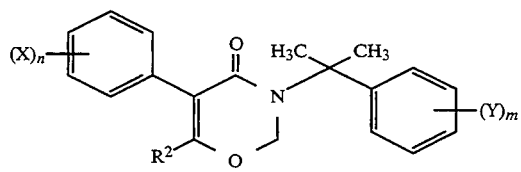

| Compound No. | (X) n | (Y) m | R² | Melting Point [°C.] |
|---|---|---|---|---|
| 107 | 2-Me, 3-Me | 3-Cl | Me | |
| 108 | 2-Me, 4-Me | 3-Cl | Me | |
| 109 | 2-Me, 5-Me | 3-Cl | Me | |
| 110 | 2-Me, 6-Me | 3-Cl | Me | |
| 111 | 3-Me, 4-Me | 3-Cl | Me | |
| 112 | 3-Me, 5-Me | 3-Cl | Me | |
| 113 | 2-Me, 4-Me, 6-Me | 3-Cl | Me | |
| 114 | 2-Me, 3-Me, 4-Me, 5-Me, 6-Me | 3-Cl | Me | |
| 115 | 2-Et | 3-Cl | Me | |
| 116 | 3-Et | 3-Cl | Me | |
| 117 | 4-Et | 3-Cl | Me | |
| 118 | 2-Pr | 3-Cl | Me | |
| 119 | 3-Pr | 3-Cl | Me | |
| 120 | 4-Pr | 3-Cl | Me | |
| 121 | 2-iPr | 3-Cl | Me | |
| 122 | 3-iPr | 3-Cl | Me | |
| 123 | 4-iPr | 3-Cl | Me | |
| 124 | 2-Bu | 3-Cl | Me | |
| 125 | 3-Bu | 3-Cl | Me | |
| 126 | 4-Bu | 3-Cl | Me | |
| 127 | 2-iBu | 3-Cl | Me | |
| 128 | 3-sBu | 3-Cl | Me | |
| 129 | 4-tBu | 3-Cl | Me | |
| 130 | 2-Hex | 3-Cl | Me | |
| 131 | 3-Hex | 3-Cl | Me | |
| 132 | 4-Hex | 3-Cl | Me | |
| 133 | 2-F, 3-Me | 3-Cl | Me | |
| 134 | 2-Cl, 3-Me, 4-Cl | 3-Cl | Me | |
| 135 | 2-OMe | 3-Cl | Me | 83.5–88.0 |
| 136 | 3-OMe | 3-Cl | Me | |
| 137 | 4-OMe | 3-Cl | Me | |
| 138 | 2-OMe, 4-OMe | 3-Cl | Me | |
| 139 | 2-OMe, 5-OMe | 3-Cl | Me | |
| 140 | 2-OMe, 6-OMe | 3-Cl | Me | |
| 141 | 3-OMe, 5-OMe | 3-Cl | Me | |
| 142 | 3-OMe, 4-OMe, 5-OMe | 3-Cl | Me | |
| 143 | 2-OEt | 3-Cl | Me | |
| 144 | 3-OEt | 3-Cl | Me | |
| 145 | 4-OEt | 3-Cl | Me | |
| 146 | 2-OPr | 3-Cl | Me | |
| 147 | 3-OPr | 3-Cl | Me | |
| 148 | 4-OPr | 3-Cl | Me | |
| 149 | 2-OiPr | 3-Cl | Me | |
| 150 | 3-OiPr | 3-Cl | Me | |
| 151 | 4-OiPr | 3-Cl | Me | |
| 152 | 2-OBu | 3-Cl | Me | |
| 153 | 3-OBu | 3-Cl | Me | |
| 154 | 4-OBu | 3-Cl | Me | |
| 155 | 2-OiBu | 3-Cl | Me | |
| 156 | 3-OsBu | 3-Cl | Me | |
| 157 | 4-OtBu | 3-Cl | Me | |
| 158 | 2-OHex | 3-Cl | Me | |
| 159 | 3-OHex | 3-Cl | Me | |
| 160 | 4-OHex | 3-Cl | Me | |
| 161 | 2-CF₃ | 3-Cl | Me | 110.0–113.5 |
| 162 | 3-CF₃ | 3-Cl | Me | 94.5–98.5 |
| 163 | 4-CF₃ | 3-Cl | Me | |
| 164 | 3-CF₃, 5-CF₃ | 3-Cl | Me | |
| 165 | 2-CH₂CF₃ | 3-Cl | Me | |
| 166 | 2-CF₂CF₃ | 3-Cl | Me | |
| 167 | 2-NO₂ | 3-Cl | Me | |
| 168 | 3-NO₂ | 3-Cl | Me | |
| 169 | 4-NO₂ | 3-Cl | Me | |
| 170 | 2-NO₂, 4-NO₂ | 3-Cl | Me | |
| 171 | 2-CF₃, 4-NO₂ | 3-Cl | Me | |
| 172 | — | 2-F | Me | |
| 173 | 2-F | 2-F | Me | |
| 174 | 2-Cl | 2-F | Me | |
| 175 | 2-Me | 2-F | Me | |
| 176 | — | 3-F | Me | 103.5–106.0 |

TABLE 1-continued

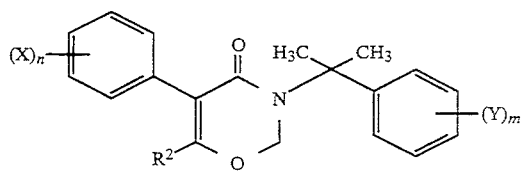

| Compound No. | (X) n | (Y) m | R² | Melting Point [°C.] |
|---|---|---|---|---|
| 177 | 2-F | 3-F | Me | 92.0–94.5 |
| 178 | 3-F | 3-F | Me | |
| 179 | 4-F | 3-F | Me | |
| 180 | 2-Cl | 3-F | Me | 138.0–139.5 |
| 181 | 3-Cl | 3-F | Me | |
| 182 | 4-Cl | 3-F | Me | |
| 183 | 3-F, 5-F | 3-F | Me | |
| 184 | 2-F, 4-F, 6-F | 3-F | Me | |
| 185 | 2-Cl, 4-Cl | 3-F | Me | |
| 186 | 3-Cl, 5-Cl | 3-F | Me | |
| 187 | 2-Me | 3-F | Me | 119.0–120.5 |
| 188 | 3-Me | 3-F | Me | |
| 189 | 4-Me | 3-F | Me | |
| 190 | 2-Me, 4-Me | 3-F | Me | |
| 191 | 3-Me, 5-Me | 3-F | Me | |
| 192 | 2-Me, 4-Me, 6-Me | 3-F | Me | |
| 193 | 4-iPr | 3-F | Me | |
| 194 | 3-Bu | 3-F | Me | |
| 195 | 2-iBu | 3-F | Me | |
| 196 | 3-sBu | 3-F | Me | |
| 197 | 4-tBu | 3-F | Me | |
| 198 | 4-Hex | 3-F | Me | |
| 199 | 2-F, 3-Me | 3-F | Me | |
| 200 | 2-Cl, 3-Me, 4-Cl | 3-F | Me | |
| 201 | 2-OMe | 3-F | Me | |
| 202 | 3-OMe | 3-F | Me | |
| 203 | 4-OMe | 3-F | Me | |
| 204 | 3-OMe, 5-OMe | 3-F | Me | |
| 205 | 3-OMe, 4-OMe, 5-OMe | 3-F | Me | |
| 206 | 2-OEt | 3-F | Me | |
| 207 | 3-OiPr | 3-F | Me | |
| 208 | 2-CF₃ | 3-F | Me | 128.0–131.0 |
| 209 | 3-CF₃ | 3-F | Me | |
| 210 | 4-CF₃ | 3-F | Me | |
| 211 | 3-CF₃, 5-CF₃ | 3-F | Me | |
| 212 | 2-NO₂ | 3-F | Me | |
| 213 | 3-NO₂ | 3-F | Me | |
| 214 | 4-NO₂ | 3-F | Me | |
| 215 | 2-NO₂, 4-NO₂ | 3-F | Me | |
| 216 | 2-CF₃, 4-NO₂ | 3-F | Me | |
| 217 | — | 4-F | Me | 89.0–93.0 |
| 218 | 2-F | 4-F | Me | |
| 219 | 2-Cl | 4-F | Me | |
| 220 | 2-Me | 4-F | Me | |
| 221 | — | 2-Cl | Me | 128.0–130.5 |
| 222 | 2-F | 2-Cl | Me | |
| 223 | 2-Cl | 2-Cl | Me | |
| 224 | 2-Me | 2-Cl | Me | |
| 225 | — | 4-Cl | Me | 73.0–77.0 |
| 226 | 2-F | 4-Cl | Me | |
| 227 | 2-Cl | 4-Cl | Me | |
| 228 | 2-Me | 4-Cl | Me | |
| 229 | — | 2-Br | Me | |
| 230 | — | 3-Br | Me | Oily |
| 231 | — | 4-Br | Me | |
| 232 | 2-F | 3-Br | Me | 59.0–66.0 |
| 233 | — | 3-I | Me | Oily |
| 234 | — | 4-I | Me | |
| 235 | — | 3-Br, 4-OMe, 5-Br | Me | 163.0–163.5 |
| 236 | 2-F | 3-Br, 4-OMe, 5-Br | Me | 167.5–169.5 |
| 237 | — | 2-F, 5-F | Me | |
| 238 | — | 2-F, 6-F | Me | |
| 239 | — | 3-F, 4-F | Me | |
| 240 | — | 3-F, 5-F | Me | |
| 241 | — | 2-F, 4-F, 6-F | Me | |
| 242 | — | 2-F, 3-F, 4-F, 5-F, 6-F | Me | |
| 243 | — | 2-Cl, 3-Cl | Me | 113.0–116.0 |
| 244 | — | 2-Cl, 4-Cl | Me | |
| 245 | — | 2-Cl, 5-Cl | Me | |
| 246 | — | 2-Cl, 6-Cl | Me | |

TABLE 1-continued

| Compound No. | (X) n | (Y) m | R² | Melting Point [°C.] |
|---|---|---|---|---|
| 247 | — | 3-Cl, 4-Cl | Me | 106.5–109.0 |
| 248 | — | 3-Cl, 5-Cl | Me | 148.0–150.5 |
| 249 | 2-Cl | 3-Cl, 5-Cl | Me | 120.5-122.5 |
| 250 | 3-Cl | 3-Cl, 5-Cl | Me | |
| 251 | 4-Cl | 3-Cl, 5-Cl | Me | |
| 252 | 2-Me | 3-Cl, 5-Cl | Me | 109.5–112.5 |
| 253 | 2-F | 3-Cl, 5-Cl | Me | 140.0–142.0 |
| 254 | 3-F | 3-Cl, 5-Cl | Me | |
| 255 | — | 2-Cl, 4-Cl, 6-Cl | Me | |
| 256 | — | 3-Cl, 4-Cl, 5-Cl | Me | 162.0–162.5 |
| 257 | 2-F | 3-Cl, 4-Cl, 5-Cl | Me | 163.0–163.5 |
| 258 | — | 2-Cl, 3-Cl, 4-Cl, 5-Cl, 6-Cl | Me | |
| 259 | — | 2-Me | Me | |
| 260 | 2-F | 2-Me | Me | |
| 261 | 2-Cl | 2-Me | Me | |
| 262 | 2-Me | 2-Me | Me | |
| 263 | — | 3-Me | Me | Oily |
| 264 | 2-F | 3-Me | Me | |
| 265 | 3-F | 3-Me | Me | |
| 266 | 4-F | 3-Me | Me | |
| 267 | 2-Cl | 3-Me | Me | 96.0–98.0 |
| 268 | 3-Cl | 3-Me | Me | |
| 269 | 4-Cl | 3-Me | Me | |
| 270 | 3-F, 5-F | 3-Me | Me | |
| 271 | 2-F, 4-F, 6-F | 3-Me | Me | |
| 272 | 2-Cl, 4-Cl | 3-Me | Me | |
| 273 | 3-Cl, 5-Cl | 3-Me | Me | |
| 274 | 2-Me | 3-Me | Me | 74.0–76.5 |
| 275 | 3-Me | 3-Me | Me | |
| 276 | 4-Me | 3-Me | Me | |
| 277 | 2-Me, 4-Me | 3-Me | Me | |
| 278 | 3-Me, 5-Me | 3-Me | Me | |
| 279 | 2-OMe | 3-Me | Me | |
| 280 | 3-OMe | 3-Me | Me | |
| 281 | 4-OMe | 3-Me | Me | |
| 282 | 2-CF₃ | 3-Me | Me | |
| 283 | 3-CF₃ | 3-Me | Me | Oily |
| 284 | 4-CF₃ | 3-Me | Me | |
| 285 | 3-CF₃, 5-CF₃ | 3-Me | Me | |
| 286 | 4-NO₂ | 3-Me | Me | |
| 287 | — | 4-Me | Me | |
| 288 | 2-F | 4-Me | Me | |
| 289 | 2-Cl | 4-Me | Me | |
| 290 | — | 3-Cl, 4-Me | Me | 86.0–87.5 |
| 291 | — | 2-Me, 3-Me | Me | |
| 292 | — | 2-Me, 4-Me | Me | |
| 293 | — | 2-Me, 5-Me | Me | |
| 294 | — | 2-Me, 6-Me | Me | |
| 295 | — | 3-Me, 4-Me | Me | |
| 296 | — | 3-Me, 5-Me | Me | 123.5–127.0 |
| 297 | — | 2-Me, 4-Me, 6-Me | Me | |
| 298 | — | 2-Me, 3-Me, 4-Me, 5-Me, 6-Me, | Me | |
| 299 | — | 2-Et | Me | |
| 300 | — | 3-Et | Me | |
| 301 | — | 4-Et | Me | |
| 302 | — | 2-Pr | Me | |
| 303 | — | 3-Pr | Me | |
| 304 | — | 4-Pr | Me | |
| 305 | — | 2-iPr | Me | |
| 306 | — | 3-iPr | Me | |
| 307 | — | 4-iPr | Me | |
| 308 | — | 2-Bu | Me | |
| 309 | — | 3-Bu | Me | |
| 310 | — | 4-Bu | Me | |
| 311 | — | 2-iBu | Me | |
| 312 | — | 3-sBu | Me | |
| 313 | — | 4-tBu | Me | |
| 314 | — | 2-Hex | Me | |
| 315 | — | 3-Hex | Me | |

TABLE 1-continued

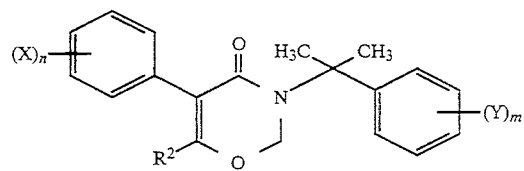

| Compound No. | (X) n | (Y) m | R² | Melting Point [°C.] |
|---|---|---|---|---|
| 316 | — | 4-Hex | Me | |
| 317 | — | 2-F, 3-Me | Me | |
| 318 | — | 2-Cl, 3-Me, 4-Cl | Me | |
| 319 | — | 2-OMe | Me | |
| 320 | 2-F | 2-OMe | Me | |
| 321 | — | 3-Cl, 4-OMe, 5-Cl | Me | 149.5–151.5 |
| 322 | 2-F | 3-Cl, 4-OMe, 5-Cl | Me | 149.0–152.5 |
| 323 | — | 3-OMe | Me | Oily |
| 324 | 2-F | 3-OMe | Me | Oily |
| 325 | 2-Cl | 3-OMe | Me | Oily |
| 326 | 2-Me | 3-OMe | Me | |
| 327 | — | 4-OMe | Me | |
| 328 | 2-F | 4-OMe | Me | |
| 329 | 2-Cl | 4-OMe | Me | |
| 330 | — | 3-Cl, 4-OMe | Me | Oily |
| 331 | — | 2-OMe, 4-OMe | Me | |
| 332 | — | 2-OMe, 5-OMe | Me | |
| 333 | — | 2-OMe, 6-OMe | Me | |
| 334 | — | 3-OMe, 5-OMe | Me | |
| 335 | — | 3-OMe, 4-OMe, 5-OMe | Me | |
| 336 | — | 2-OEt | Me | |
| 337 | — | 3-OEt | Me | |
| 338 | — | 4-OEt | Me | |
| 339 | — | 2-OPr | Me | |
| 340 | — | 3-OPr | Me | |
| 341 | — | 4-OPr | Me | |
| 342 | — | 2-OiPr | Me | |
| 343 | — | 3-OiPr | Me | |
| 244 | — | 4-OiPr | Me | |
| 345 | — | 2-OBu | Me | |
| 346 | — | 3-OBu | Me | |
| 347 | — | 4-OBu | Me | |
| 348 | — | 2-OiBu | Me | |
| 349 | — | 3-OsBu | Me | |
| 350 | — | 4-OtBu | Me | |
| 351 | — | 2-OHex | Me | |
| 352 | — | 3-OHex | Me | |
| 353 | — | 4-OHex | Me | |
| 354 | — | 2-CF₃ | Me | |
| 355 | 2-F | 2-CF₃ | Me | |
| 356 | 2-Cl | 2-CF₃ | Me | |
| 357 | 2-Me | 2-CF₃ | Me | |
| 358 | — | 3-CF₃ | Me | 67.5–72.0 |
| 359 | 2-F | 3-CF₃ | Me | 71.5–76.0 |
| 360 | 2-Cl | 3-CF₃ | Me | Oily |
| 361 | 3-Cl | 3-CF₃ | Me | |
| 362 | 4-Cl | 3-CF₃ | Me | |
| 363 | 2-Me | 3-CF₃ | Me | 75.0–78.0 |
| 364 | 3-Me | 3-CF₃ | Me | |
| 365 | 3-CF₃ | 3-CF₃ | Me | Oily |
| 366 | — | 4-CF₃ | Me | |
| 367 | 2-F | 4-CF₃ | Me | |
| 368 | 2-Cl | 4-CF₃ | Me | |
| 369 | 2-Me | 4-CF₃ | Me | |
| 370 | — | 3-CF₃, 5-CF₃ | Me | 122.0–123.0 |
| 371 | — | 2-CH₂CF₃ | Me | |
| 372 | — | 2-CF₂CF₃ | Me | |
| 373 | — | 2-OCHF₂ | Me | |
| 374 | — | 3-OCHF₂ | Me | Oily |
| 375 | 2-F | 3-OCHF₂ | Me | 69.0–73.5 |
| 376 | 2-Cl | 3-OCHF₂ | Me | Oily |
| 377 | 3-Cl | 3-OCHF₂ | Me | |
| 378 | 4-Cl | 3-OCHF₂ | Me | |
| 379 | 2-Me | 3-OCHF₂ | Me | |
| 380 | 3-Me | 3-OCHF₂ | Me | |
| 381 | 4-Me | 3-OCHF₂ | Me | |
| 382 | — | 4-OCHF₂ | Me | |
| 383 | — | 3-OCH₂CF₂CF₃ | Me | |
| 384 | — | 3-OCH₂CH₂Cl | Me | |
| 385 | — | 3-OCF₂CHCl₂ | Me | |

TABLE 1-continued

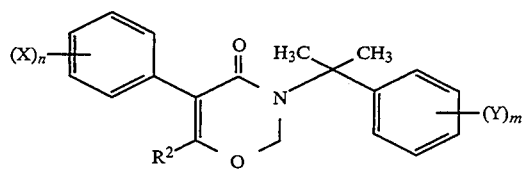

| Compound No. | (X) n | (Y) m | R² | Melting Point [°C.] |
|---|---|---|---|---|
| 386 | — | 3-OCF₂CHF₂ | Me | |
| 387 | — | 3-OCF₂CH₂Cl | Me | |
| 388 | — | — | H | Oily |
| 389 | 2-F | — | H | |
| 390 | 2-Cl | — | H | |
| 391 | 2-Me | — | H | |
| 392 | — | 3-Cl | H | Oily |
| 393 | 2-F | 3-Cl | H | |
| 394 | 2-Cl | 3-Cl | H | |
| 395 | 2-Me | 3-Cl | H | |
| 396 | — | 3-Me | H | |
| 397 | 2-F | 3-Me | H | |
| 398 | — | 3-CF₃ | H | |
| 399 | 2-F | 3-CF₃ | H | |
| 400 | — | 3-OCHF₂ | H | |
| 401 | — | 3-Cl, 5-Cl | H | |
| 402 | — | — | Et | 49.0–51.0 |
| 403 | — | 3-Cl | Et | Oily |
| 404 | 2-F | 3-Cl | Et | |
| 405 | 2-Cl | 3-Cl | Et | |
| 406 | 2-Me | 3-Cl | Et | |
| 407 | — | 3-Me | Et | |
| 408 | 2-F | 3-Me | Et | |
| 409 | 2-Cl | 3-Me | Et | |
| 410 | 2-Me | 3-Me | Et | |
| 411 | — | 3-CF₃ | Et | |
| 412 | 2-F | 3-CF₃ | Et | |
| 413 | 2-Cl | 3-CF₃ | Et | |
| 414 | 2-Me | 3-CF₃ | Et | |
| 415 | — | 3-OCHF₂ | Et | |
| 416 | 2-F | 3-OCHF₂ | Et | |
| 417 | 2-Cl | 3-OCHF₂ | Et | |
| 418 | — | 3-Br, 4-OMe, 5-Br | Et | 154.5–155.5 |
| 419 | — | 3-Cl, 5-Cl | Et | |
| 420 | 2-F | 3-Cl, 5-Cl | Et | |
| 421 | — | — | Pr | Oily |
| 422 | — | 3-Cl | Pr | Oily |
| 423 | 2-F | 3-Cl | Pr | |
| 424 | 2-Cl | 3-Cl | Pr | |
| 425 | 2-Me | 3-Cl | Pr | |
| 426 | — | 3-Me | Pr | |
| 427 | 2-F | 3-Me | Pr | |
| 428 | 2-Cl | 3-Me | Pr | |
| 429 | 2-Me | 3-Me | Pr | |
| 430 | — | 3-CF₃ | Pr | |
| 431 | 2-F | 3-CF₃ | Pr | |
| 432 | 2-Cl | 3-CF₃ | Pr | |
| 433 | 2-Me | 3-CF₃ | Pr | |
| 434 | — | 3-OCHF₂ | Pr | |
| 435 | 2-F | 3-OCHF₂ | Pr | |
| 436 | 2-Cl | 3-OCHF₂ | Pr | |
| 437 | 2-Me | 3-OCHF₂ | Pr | |
| 438 | — | 3-Cl, 5-Cl | Pr | |
| 439 | 2-F | 3-Cl, 5-Cl | Pr | |
| 440 | — | — | iPr | Oily |
| 441 | — | 3-Cl | ipr | |
| 442 | 2-F | 3-Cl | iPr | |
| 443 | 2-Cl | 3-Cl | iPr | |
| 444 | 2-Me | 3-Cl | iPr | |
| 445 | — | 3-Me | iPr | |
| 446 | 2-F | 3-Me | iPr | |
| 447 | 2-Cl | 3-Me | iPr | |
| 448 | 2-Me | 3-Me | iPr | |
| 449 | — | 3-CF₃ | iPr | |
| 450 | 2-F | 3-CF₃ | iPr | |
| 451 | 2-Cl | 3-CF₃ | iPr | |
| 452 | 2-Me | 3-CF₃ | iPr | |
| 453 | — | 3-OCHF₂ | iPr | |
| 454 | 2-F | 3-OCHF₂ | iPr | |
| 455 | 2-Cl | 3-OCHF₂ | iPr | |

TABLE 1-continued

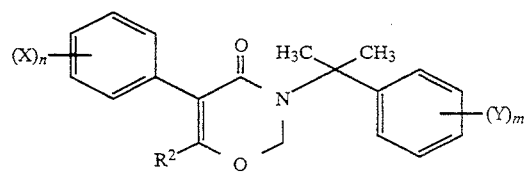

| Compound No. | (X) n | (Y) m | $R^2$ | Melting Point [°C.] |
|---|---|---|---|---|
| 456 | 2-Me | 3-OCHF$_2$ | iPr | |
| 457 | — | 3-Cl, 5-Cl | iPr | |
| 458 | 2-F | 3-Cl, 5-Cl | iPr | |
| 459 | — | — | Bu | |
| 460 | — | 3-Cl | Bu | |
| 461 | 2-F | 3-Cl | Bu | |
| 462 | 2-Cl | 3-Cl | Bu | |
| 463 | 2-Me | 3-Cl | Bu | |
| 464 | — | 3-Me | Bu | |
| 465 | 2-F | 3-Me | Bu | |
| 466 | 2-Cl | 3-Me | Bu | |
| 467 | 2-Me | 3-Me | Bu | |
| 468 | — | 3-CF$_3$ | Bu | |
| 469 | 2-F | 3-CF$_3$ | Bu | |
| 470 | 2-Cl | 3-CF$_3$ | Bu | |
| 471 | 2-Me | 3-CF$_3$ | Bu | |
| 472 | — | 3-OCHF$_2$ | Bu | |
| 473 | 2-F | 3-OCHF$_2$ | Bu | |
| 474 | 2-Cl | 3-OCHF$_2$ | Bu | |
| 475 | 2-Me | 3-OCHF$_2$ | Bu | |
| 476 | — | 3-Cl, 5-Cl | Bu | |
| 477 | 2-F | 3-Cl, 5-Cl | Bu | |
| 478 | — | — | $^nC_5H_{11}$ | |
| 479 | — | 3-Cl | $^nC_5H_{11}$ | |
| 480 | 2-F | 3-Cl | $^nC_5H_{11}$ | |
| 481 | — | 3-CF$_3$ | $^nC_5H_{11}$ | |
| 482 | 2-F | 3-CF$_3$ | $^nC_5H_{11}$ | |
| 483 | — | 3-Me | $^nC_5H_{11}$ | |
| 484 | 2-F | 3-Me | $^nC_5H_{11}$ | |
| 485 | — | 3-OCHF$_2$ | $^nC_5H_{11}$ | |
| 486 | 2-F | 3-OCHF$_2$ | $^nC_5H_{11}$ | |
| 487 | — | 3-Cl, 5-Cl | $^nC_5H_{11}$ | |
| 488 | — | 3-Cl | iBu | |
| 489 | — | 3-CF$_3$ | iBu | |
| 490 | — | 3-OCHF$_2$ | iBu | |
| 491 | — | 3-Cl, 5-Cl | iBu | |
| 492 | — | 3-Cl | sBu | |
| 493 | — | 3-CF$_3$ | sBu | |
| 494 | — | 3-OCHF$_2$ | sBu | |
| 495 | — | 3-Cl | tBu | |
| 496 | — | 3-Cl | Hex | |
| 497 | — | 3-CF$_3$ | Hex | |
| 498 | — | 3-OCHF$_2$ | Hex | |
| 499 | — | 3-Cl, 5-Cl | Hex | |

TABLE 2

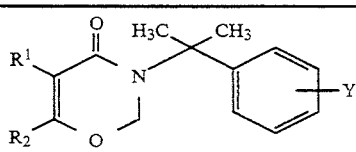

| Compound No. | $R^1$ | Y | $R^2$ | Melting Point [°C.] |
|---|---|---|---|---|
| 500 | Me | — | Me | |
| 501 | Et | — | Me | |
| 502 | Pr | — | Me | |
| 503 | iPr | — | Me | |
| 504 | Bu | — | Me | |
| 505 | iBu | — | Me | 63.0–67.0 |
| 506 | sBu | — | Me | |
| 507 | tBu | — | Me | |
| 508 | Hex | — | Me | |
| 509 | Me | 3-Cl | Me | |
| 510 | Et | 3-Cl | Me | |
| 511 | Pr | 3-Cl | Me | |

TABLE 2-continued

| Compound No. | R¹ | Y | R² | Melting Point [°C.] |
|---|---|---|---|---|
| 512 | iPr | 3-Cl | Me | |
| 513 | Bu | 3-Cl | Me | |
| 514 | iBu | 3-Cl | Me | 70.5–74.0 |
| 515 | sBu | 3-Cl | Me | |
| 516 | tBu | 3-Cl | Me | |
| 517 | Hex | 3-Cl | Me | |
| 518 | iPr | 3-F | Me | |
| 519 | iBu | 3-F | Me | |
| 520 | sBu | 3-F | Me | |
| 521 | tBu | 3-F | Me | |
| 522 | iPr | 3-OCHF₂ | Me | |
| 523 | iBu | 3-OCHF₂ | Me | |
| 524 | sBu | 3-OCHF₂ | Me | |
| 525 | tBu | 3-OCHF₂ | Me | |
| 526 | iPr | 3-Cl | H | |
| 527 | iBu | 3-Cl | H | |
| 528 | sBu | 3-Cl | H | |
| 529 | tBu | 3-Cl | H | |
| 530 | iPr | 3-Cl | Et | |
| 531 | iBu | 3-Cl | Et | |
| 532 | sBu | 3-Cl | Et | |
| 533 | tBu | 3-Cl | Et | |
| 534 | iBu | 3-Cl | iPr | |
| 535 | iBu | 3-Cl | iPr | |
| 536 | iBu | 3-Cl | Bu | |
| 537 | iBu | 3-Cl | iBu | |
| 538 | iBu | 3-Cl | sBu | |
| 539 | iBu | 3-Cl | tBu | |
| 540 | iBu | 3-Cl | Hex | |
| 541 | CH₂=CH— | — | Me | |
| 542 | CH₂=CH— | 3-Cl | Me | |
| 543 | CH₂=CH— | 3-Cl, 5-Cl | Me | |
| 544 | CH₃—CH=CH— | — | Me | |
| 545 | CH₃—CH=CH— | 3-Cl | Me | |
| 546 | CH₃—CH=CH— | 3-Cl, 5-Cl | Me | |
| 547 | CH₂=C(CH₃)— | — | Me | |
| 548 | CH₂=C(CH₃)— | 3-Cl | Me | |
| 549 | CH₂=C(CH₃)— | 3-Cl, 5-Cl | Me | |
| 550 | CH₂=CH—CH=CH— | — | Me | |
| 551 | CH₂=CH—CH=CH— | 3-Cl | Me | |
| 552 | CH₂=CH—CH=CH— | 3-Cl, 5-Cl | Me | |
| 553 | CH₃—CH=CH—CH=CH— | — | Me | |
| 554 | CH₃—CH=CH—CH=CH— | 3-Cl | Me | |
| 555 | CH₃—CH=CH—CH=CH— | 3-Cl, 5-Cl | Me | |
| 556 | (CH₃)₂C=CH— | — | Me | |
| 557 | (CH₃)₂C=CH— | 3-Cl | Me | |
| 558 | (CH₃)₂C=CH— | 3-Cl, 5-Cl | Me | |
| 559 | CH₂=CH—CH₂— | — | Me | |
| 560 | CH₂=CH—CH₂— | 3-Cl | Me | |
| 561 | CH₂=CH—CH₂— | 3-Cl, 5-Cl | Me | |
| 562 | CH₂=C(CH₃)—CH₂— | — | Me | |
| 563 | CH₂=C(CH₃)—CH₂— | 3-Cl | Me | |
| 564 | CH₂=C(CH₃)—CH₂— | 3-Cl, 5-Cl | Me | |
| 565 | HC≡C— | — | Me | |
| 566 | HC≡C— | 3-Cl | Me | |
| 567 | HC≡C— | 3-Cl, 5-Cl | Me | 122.0–127.0 |
| 568 | CH₃—C≡C— | — | Me | |
| 569 | CH₃—C≡C— | 3-Cl | Me | |
| 570 | CH₃—C≡C— | 3-Cl, 5-Cl | Me | |
| 571 | HC≡C—CH₂— | — | Me | |
| 572 | HC≡C—CH₂— | 3-Cl | Me | |
| 573 | HC≡C—CH₂— | 3-Cl, 5-Cl | Me | |
| 574 | HC≡C—CH(CH₃)— | — | Me | |
| 575 | HC≡C—CH(CH₃)— | 3-Cl | Me | |
| 576 | HC≡C—CH(CH₃)— | 3-Cl, 5-Cl | Me | |

TABLE 3

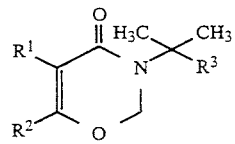

| Compound No. | R¹ | R³ | R² | Melting Point [°C.] |
|---|---|---|---|---|
| 600 | 2-naphthyl | Ph | Me | |
| 601 | 2-naphthyl | 3-Cl-phenyl | Me | |
| 602 | 1-naphthyl | Ph | Me | |
| 603 | 1-naphthyl | 3-Cl-phenyl | Me | |
| 604 | 3-Cl-2-naphthyl | 3-Cl-phenyl | Me | |
| 605 | 3-F-2-naphthyl | 3-Cl-phenyl | Me | |
| 606 | Ph | 2-naphthyl | Me | 77.0–81.0 |
| 607 | 2-Cl-phenyl | 2-naphthyl | Me | |
| 608 | Ph | 1-naphthyl | Me | |
| 609 | 2-Cl-phenyl | 1-naphthyl | Me | |
| 610 | Ph | 4-Cl-2-naphthyl | Me | |
| 611 | 3-Cl-2-naphthyl | 4-Cl-2-naphthyl | Me | |
| 612 | Ph | 4-Cl-2-naphthyl | H | |
| 613 | α-methylbenzyl | Ph | Me | |
| 614 | α-methylbenzyl | 3-Cl-phenyl | Me | |

TABLE 3-continued

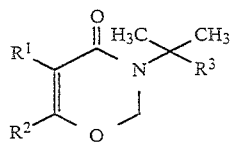

| Compound No. | R¹ | R³ | R² | Melting Point [°C.] |
|---|---|---|---|---|
| 615 | α-methylbenzyl | 3-OCHF₂-phenyl | Me | |
| 616 | α-methylbenzyl | 3-F-phenyl | Me | |
| 617 | α-methylbenzyl | 3-OMe-phenyl | Me | |
| 618 | α-methylbenzyl | 3-CF₃-phenyl | Me | |
| 619 | α-methylbenzyl | 3-Me-phenyl | Me | |
| 620 | α-methylbenzyl | 3,5-diCl-phenyl | Me | |
| 621 | cumyl | Ph | Me | |
| 622 | cumyl | 3-Cl-phenyl | Me | |
| 623 | cumyl | 3-OCHF₂-phenyl | Me | |
| 624 | cumyl | 3-F-phenyl | Me | |
| 625 | cumyl | 3-OMe-phenyl | Me | |
| 626 | cumyl | 3-CF₃-phenyl | Me | |
| 627 | cumyl | 3-Me-phenyl | Me | |
| 628 | cumyl | 3,5-diCl-phenyl | Me | |

TABLE 3-continued

| Compound No. | R¹ | R³ | R² | Melting Point [°C.] |
|---|---|---|---|---|
| 629 | Me₂C(Ph)- | 4-Cl-C₆H₄- | Me | |
| 630 | Me₂C(Ph)- | 4-F-C₆H₄- | Me | |
| 650 | Ph | Me | H | |
| 651 | Ph | Et | H | |
| 652 | Ph | Pr | H | |
| 653 | Ph | iPr | H | |
| 654 | Ph | Bu | H | |
| 655 | Ph | iBu | H | |
| 656 | Ph | sBu | H | |
| 657 | Ph | tBu | H | |
| 658 | Ph | Hex | H | |
| 659 | Ph | Me | Me | |
| 660 | Ph | Et | Me | |
| 661 | Ph | Pr | Me | |
| 662 | Ph | iPr | Me | |
| 663 | Ph | Bu | Me | |
| 664 | Ph | iBu | Me | |
| 665 | Ph | sBu | Me | |
| 666 | Ph | tBu | Me | 68.0–73.0 |
| 667 | Ph | Hex | Me | |
| 668 | Ph | Me | Et | |
| 669 | Ph | Et | Et | |
| 670 | Ph | Pr | Et | |
| 671 | Ph | iPr | Et | |
| 672 | Ph | Bu | Et | |
| 673 | Ph | iBu | Et | |
| 674 | Ph | sBu | Et | |
| 675 | Ph | tBu | Et | |
| 676 | Ph | Hex | Et | |
| 700 | Ph | CH₂Ph | Me | Oily |
| 701 | Ph | 2-Et-6-Me-C₆H₃- | Me | |
| 702 | Ph | 3-Et-5-Me-C₆H₃- | Me | |
| 703 | Ph | 4-Et-3-Me-C₆H₃- | Me | |
| 704 | Ph | 2-Et-6-Cl-C₆H₃- | Me | |
| 705 | Ph | 3-Et-5-Cl-C₆H₃- | Me | |
| 706 | Ph | 4-Et-3-Cl-C₆H₃- | Me | |
| 707 | Ph | 2,4-diCl-5-Et-C₆H₂- | Me | |
| 708 | Ph | 3,5-diCl-C₆H₃- | Me | |
| 709 | Ph | 2-(1-methylethyl)phenyl | Me | |
| 710 | Ph | n-Pr-C₆H₅ | Me | |
| 711 | Ph | 2-Me-6-Pr-C₆H₃- | Me | |
| 712 | Ph | 3-Me-5-Pr-C₆H₃- | Me | |
| 713 | Ph | 4-Me-3-Pr-C₆H₃- | Me | |
| 714 | Ph | sBu-C₆H₅ | Me | |
| 715 | Ph | iBu-C₆H₅ | Me | |
| 716 | Ph | 2-Cl-6-Pr-C₆H₃- | Me | |
| 717 | Ph | 3-Cl-5-Pr-C₆H₃- | Me | |
| 718 | Ph | 4-Cl-3-Pr-C₆H₃- | Me | |

TABLE 6

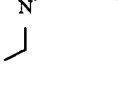

| Compound No. | R⁴ | R⁵ | Y | R² | Melting Point [°C.] |
|---|---|---|---|---|---|
| 800 | Et | Me | — | Me | |
| 801 | Et | Me | 3-Cl | Me | 71.0–74.0 |
| 802 | Et | Me | 3-Cl, 5-Cl | Me | |
| 803 | Et | Me | 3-CF₃ | Me | |
| 804 | Et | Me | 3-OCHF₂ | Me | |

TABLE 6-continued

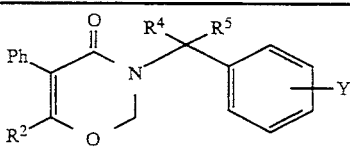

| Compound No. | R⁴ | R⁵ | Y | R² | Melting Point [°C.] |
|---|---|---|---|---|---|
| 805 | Et | Me | 3-Cl, 5-Cl | H | |
| 806 | Et | Me | — | Et | |
| 807 | Et | Me | 3-Cl | Et | |
| 808 | Et | Me | 3-Cl, 5-Cl | Et | |
| 809 | Pr | Me | — | Me | |
| 810 | Pr | Me | 3-Cl | Me | |
| 811 | Pr | Me | 3-Cl, 5-Cl | Me | |
| 812 | iPr | Me | — | Me | |
| 813 | iPr | Me | 3-Cl | Me | |
| 814 | iPr | Me | 3-Cl, 5-Cl | Me | |
| 815 | Bu | Me | — | Me | |
| 816 | iBu | Me | 3-Cl | Me | |
| 817 | sBu | Me | 3-Cl, 5-Cl | Me | |
| 818 | tBu | Me | — | Me | 68.0–72.0 |
| 819 | tBu | Me | 3-Cl | Me | |
| 820 | tBu | Me | 3-Cl, 5-Cl | Me | |
| 821 | Hex | Me | — | Me | |
| 822 | Hex | Me | 3-Cl | Me | |
| 823 | Hex | Me | 3-Cl, 5-Cl | Me | |
| 824 | Et | Et | — | Me | |
| 825 | Et | Et | 3-Cl | Me | |
| 826 | Et | Et | 3-Cl, 5-Cl | Me | |
| 827 | Pr | Et | — | Me | |
| 828 | Pr | Et | 3-Cl | Me | |
| 829 | Pr | Et | 3-Cl, 5-Cl | Me | |
| 830 | iPr | Et | — | Me | |
| 831 | iBu | Et | 3-Cl | Me | |
| 832 | sBu | Et | 3-Cl, 5-Cl | Me | |
| 833 | tBu | Et | 3-Cl | Me | |
| 834 | Pr | Pr | 3-Cl | Me | |
| 835 | iPr | Pr | 3-Cl | Me | |
| 836 | iBu | Pr | 3-Cl | Me | |
| 837 | iBu | Bu | 3-Cl | Me | |
| 838 | sBu | Bu | 3-Cl | Me | |
| 839 | tBu | Bu | 3-Cl | Me | |
| 840 | iBu | iBu | 3-Cl | Me | |
| 841 | tBu | iBu | — | Me | |
| 842 | sBu | Hex | 3-Cl | Me | |
| 843 | tBu | Hex | 3-Cl, 5-Cl | Me | |
| 844 | Hex | Hex | — | Me | |

TABLE 5

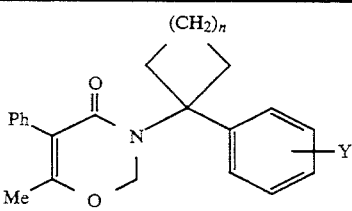

| Compound No. | n | Y | Melting Point [°C.] |
|---|---|---|---|
| 850 | 0 | — | |
| 851 | 0 | 3-Cl | |
| 852 | 0 | 3-Cl, 5-Cl | |
| 853 | 1 | — | |
| 854 | 1 | 3-Cl | |
| 855 | 1 | 3-Cl, 5-Cl | |
| 856 | 2 | — | |
| 857 | 2 | 3-Cl | 70.5–73.5 |
| 858 | 2 | 3-Cl, 5-Cl | |
| 859 | 3 | — | |
| 860 | 3 | 3-Cl | 123.0–129.0 |
| 861 | 3 | 3-Cl, 5-Cl | |
| 862 | 4 | — | |
| 863 | 4 | 3-Cl | |
| 864 | 4 | 3-Cl, 5-Cl | |

TABLE 5-continued

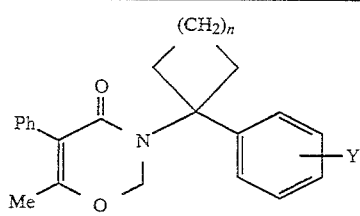

| Compound No. | n | Y | Melting Point [°C.] |
|---|---|---|---|
| 865 | 5 | — | |
| 866 | 5 | 3-Cl | |
| 867 | 5 | 3-Cl, 5-Cl | |

According to this invention, the compounds of formula (I) above can be produced, for example, by reacting compounds of general formula (II) below

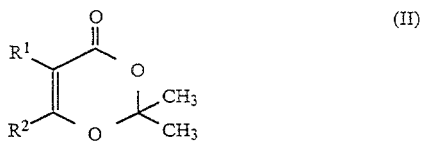
(II)

wherein R¹ and R² are as defined above, with compounds of general formula (III) below

(III)

wherein R³, R⁴ and R⁵ are as defined above.

The reaction between the compounds of formula (II) above and the compounds of formula (III) above can be carried out in a suitable solvent or without solvent at a reaction temperature which is usually between about 90° C. and about 160° C., or the boiling point of the solvent used. As the solvent, there is no limitation thereon and any one may be used so far as it is substantially inert. However, it is preferred from the viewpoint of reaction temperature to use organic solvents having high boiling points not lower than 90° C., such as toluene, xylene and mesitylene. Reaction time may vary depending on other reaction conditions used but generally the reaction may be completed in 1 to 120 minutes.

Further, there is no strict limitation for the proportions of the compounds of formula (III) to the compounds of formula (II), and it is convenient to use the compounds of formula (III) in an amount within the range of usually 0.5 to 2 moles, and particularly 0.9 to 1.1 moles, per mole of the compounds of formula (II).

Separation and purification of the compounds of formula (I) produced may be carried out by methods known per se, such as recrystallization, extraction and chromatography.

Among the compounds of formula (II) above used as starting materials in the above-described reaction, 1,3-dioxin-4-one derivatives represented by general formula (II-1) below

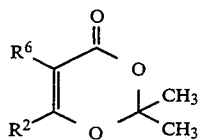

wherein $R^2$ is as defined above; and $R^6$ is a substituted aryl group are not described in prior art references and are novel compounds.

As the substituted aryl group ($R^6$) in formula (II-1) above, preferred is a phenyl group substituted with one or two substituent groups selected from the group consisting of a halogen atom, a lower alkyl group, a lower alkoxy group, a lower haloalkyl group and a nitro group.

The compounds of formula (II-1) can be produced by a method known per se, for example, the method described in Chem. Pharm. Bull., 31(6), 1895–1901 (1983).

More specifically, the compounds of formula (II-1) can be produced, for example, by reacting compounds of formula (IV) with acetone in acetic anhydride in the presence of a small amount of sulfuric acid as a catalyst in accordance with Reaction Scheme A below:

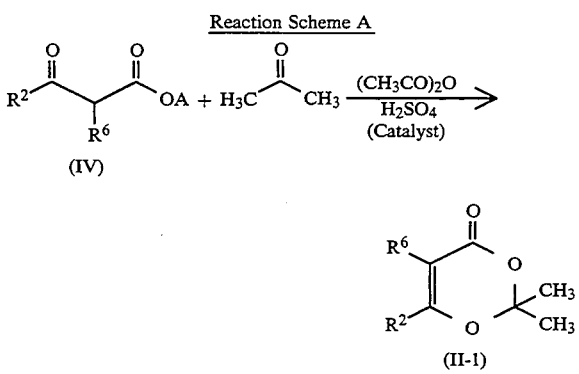

wherein $R^2$ and $R^6$ are as defined above, and

A is a hydrogen atom or a group releasable under acidic conditions, for example, a tert-butyl group. Reaction temperature is desirably within the range of from $-25°$ C. to around room temperature. The reaction temperature may vary depending on other reaction conditions, and the reaction may be completed usually in about 1 to 100 hours. Proportion of acetone used to the compounds of formula (IV) may be within the range of 1 to moles, and particularly 1.5 to 3 moles, per mole of the compounds of formula (IV). The compounds of formula (II-1) can be separated from the reaction mixture by conventional methods and readily purified by recrystallization, column chromatography and the like.

The compounds of formula (IV) used as starting materials in the above-described reaction can be produced by methods known per se or methods similar thereto.

Among the compounds of formula (III) used as starting materials for the production of the compounds of formula (I) above, N-methylene-1-methyl-1-phenylethylamine derivatives represented by general formula (III-1)

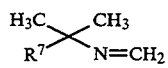

wherein $R^7$ is a substituted aryl group are not described in prior art literature and novel compounds.

As the substituted aryl group ($R^7$) in formula (III-1) above, preferred is a phenyl group substituted with 1 to 3 substituent groups selected from the group consisting of a halogen atom, a lower alkyl group, a lower alkoxy group, a lower haloalkyl group and a lower haloalkoxy group, particularly a phenyl group substituted with a halogen atom or a lower haloalkoxy group.

The compounds of formula (III-1) can be produced by methods known per se, for example, the method described in U.S. Pat. No. 2,582,128.

More specifically, the compounds of formula (III-1) can be produced by dropwise adding the compounds of formula (IV) in formalin according to Reaction Scheme B below:

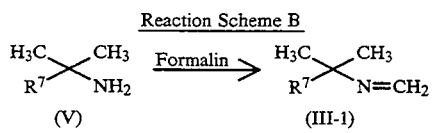

wherein $R^7$ is as defined above. Reaction temperature is desirably room temperature. Reaction time may vary depending on other reaction conditions and the reaction is completed usually in about 0.1 to 10 hours. The products of formula (III-1) can be separated from the reaction mixtures by conventional methods and readily purified by recrystallization, distillation, column chromatography, etc.

It has revealed that the compounds of formula (V) used as starting materials in the production of the compounds of formula (I) mostly are in equilibrium states with trimers represented by formula below at around room temperature and sometimes exist as mixtures therewith, or can exist in some cases as trimers alone.

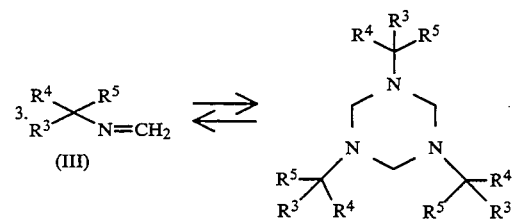

Therefore, although the compounds of formula (III) and the compounds of formula (III-1) include not only monomers but also mixtures of the above-described trimers and the monomers, they are represented herein by the structures and names of the monomers for simplification.

Specific examples of the compounds of formula (II-1) and of the novel intermediate compounds of formula (III-1) are as shown in Tables 6 and 7 below. In the tables, abbreviations have the same meanings as above.

TABLE 4

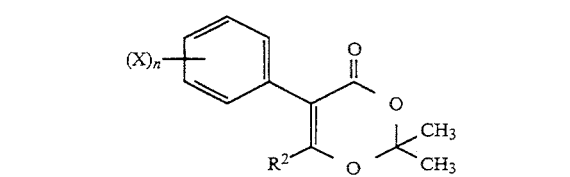

| Compound No. | X | R² | Melting Point [°C.] |
|---|---|---|---|
| 2-1 | 2-F | Me | 65.5–69.5 |
| 2-2 | 3-F | Me | Oily |
| 2-3 | 4-F | Me | 78.0–81.5 |
| 2-4 | 2-Cl | Me | 58.0–61.5 |
| 2-5 | 3-Cl | Me | Oily |
| 2-6 | 4-Cl | Me | 69.0–73.0 |
| 2-7 | 2-Br | Me | |
| 2-8 | 4-I | Me | |
| 2-9 | 2-F, 3-F | Me | |
| 2-10 | 2-F, 4-F | Me | |
| 2-11 | 2-F, 5-F | Me | |
| 2-12 | 2-F, 6-F | Me | |
| 2-13 | 3-F, 4-F | Me | |
| 2-14 | 3-F, 5-F | Me | |
| 2-15 | 2-F, 4-F, 6-F | Me | |
| 2-16 | 2-F, 3-F, 4-F, 5-F, 6-F | Me | |
| 2-17 | 2-Cl, 4-Cl | Me | |
| 2-18 | 3-Cl, 5-Cl | Me | |
| 2-19 | 2-Cl, 4-Cl, 6-Cl | Me | |
| 2-20 | 2-Cl, 3-Cl, 4-Cl, 5-Cl, 6-Cl | Me | |
| 2-21 | 2-Cl, 6-F | Me | |
| 2-22 | 2-Me | Me | 73.0–78.0 |
| 2-23 | 3-Me | Me | |
| 2-24 | 4-Me | Me | |
| 2-25 | 2-Me, 4-Me | Me | |
| 2-26 | 3-Me, 5-Me | Me | |
| 2-27 | 2-Me, 4-Me, 6-Me | Me | |
| 2-28 | 2-Et | Me | |
| 2-29 | 3-Et | Me | |
| 2-30 | 4-Et | Me | |
| 2-31 | 4-Pr | Me | |
| 2-32 | 2-iPr | Me | |
| 2-33 | 3-iPr | Me | |
| 2-34 | 4-iPr | Me | |
| 2-35 | 2-Bu | Me | |
| 2-36 | 3-Bu | Me | |
| 2-37 | 4-Bu | Me | |
| 2-38 | 2-iBu | Me | |
| 2-39 | 3-sBu | Me | |
| 2-40 | 4-tBu | Me | |
| 2-41 | 2-Hex | Me | |
| 2-42 | 4-Hex | Me | |
| 2-43 | 2-Cl, 3-Me, 4-Cl | Me | |
| 2-44 | 2-OMe | Me | 58.0–62.5 |
| 2-45 | 3-OMe | Me | |
| 2-46 | 4-OMe | Me | |
| 2-47 | 2-OMe, 4-OMe | Me | |
| 2-48 | 2-OMe, 6-OMe | Me | |
| 2-49 | 3-OMe, 5-OMe | Me | |
| 2-50 | 3-OMe, 4-OMe, 5-OMe | Me | |
| 2-51 | 2-OEt | Me | |
| 2-52 | 4-OEt | Me | |
| 2-53 | 3-OPr | Me | |
| 2-54 | 3-OiPr | Me | |
| 2-55 | 2-OBu | Me | |
| 2-56 | 4-OBu | Me | |
| 2-57 | 2-OiBu | Me | |
| 2-58 | 3-OsBu | Me | |
| 2-59 | 4-OtBu | Me | |
| 2-60 | 4-OHex | Me | |
| 2-61 | 2-CF₃ | Me | 104.0–108.0 |
| 2-62 | 3-CF₃ | Me | Oily |
| 2-63 | 4-CF₃ | Me | |
| 2-64 | 3-CF₃, 5-CF₃ | Me | |
| 2-65 | 2-CH₂CF₃ | Me | |
| 2-66 | 2-CF₂CF₃ | Me | |
| 2-67 | 2-NO₂ | Me | |
| 2-68 | 3-NO₂ | Me | |
| 2-69 | 4-NO₂ | Me | |
| 2-70 | 2-NO₂, 4-NO₂ | Me | |
| 2-71 | 2-CF₃, 4-NO₂ | Me | |

TABLE 4-continued

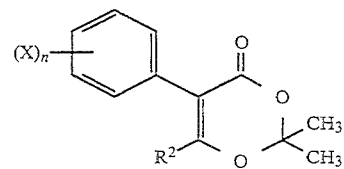

| Compound No. | X | R² | Melting Point [°C.] |
|---|---|---|---|
| 2-72 | 2-F | H | |
| 2-73 | 3-F | H | |
| 2-74 | 4-F | H | |
| 2-75 | 2-Cl | H | |
| 2-76 | 3-Cl | H | |
| 2-77 | 4-Cl | H | |
| 2-78 | 3-F, 5-F | H | |
| 2-79 | 2-F, 4-F, 6-F | H | |
| 2-80 | 2-Cl, 4-Cl | H | |
| 2-81 | 3-Cl, 5-Cl | H | |
| 2-82 | 2-Me | H | |
| 2-83 | 3-Me | H | |
| 2-84 | 4-Me | H | |
| 2-85 | 2-Me, 4-Me | H | |
| 2-86 | 3-Me, 5-Me | H | |
| 2-87 | 2-Me, 4-Me, 6-Me | H | |
| 2-88 | 4-iPr | H | |
| 2-89 | 3-Bu | H | |
| 2-90 | 2-iBu | H | |
| 2-91 | 3-sBu | H | |
| 2-92 | 4-tBu | H | |
| 2-93 | 4-Hex | H | |
| 2-94 | 2-F, 3-Me | H | |
| 2-95 | 2-Cl, 3-Me, 4-Cl | H | |
| 2-96 | 2-OMe | H | |
| 2-97 | 3-OMe | H | |
| 2-98 | 4-OMe | H | |
| 2-99 | 3-OMe, 5-OMe | H | |
| 2-100 | 3-OMe, 4-OMe, 5-OMe | H | |
| 2-101 | 2-OEt | H | |
| 2-102 | 3-OiPr | H | |
| 2-103 | 2-CF₃ | H | |
| 2-104 | 3-CF₃ | H | |
| 2-105 | 4-CF₃ | H | |
| 2-106 | 3-CF₃, 5-CF₃ | H | |
| 2-107 | 2-NO₂ | H | |
| 2-108 | 3-NO₂ | H | |
| 2-109 | 4-NO₂ | H | |
| 2-110 | 2-NO₂, 4-NO₂ | H | |
| 2-111 | 2-CF₃, 4-NO₂ | H | |
| 2-112 | 2-F | Et | |
| 2-113 | 3-F | Et | |
| 2-114 | 4-F | Et | |
| 2-115 | 2-Cl | Et | |
| 2-116 | 3-Cl | Et | |
| 2-117 | 4-Cl | Et | |
| 2-118 | 3-F, 5-F | Et | |
| 2-119 | 2-F, 4-F, 6-F | Et | |
| 2-120 | 2-Cl, 4-Cl | Et | |
| 2-121 | 3-Cl, 5-Cl | Et | |
| 2-122 | 2-Me | Et | |
| 2-123 | 3-Me | Et | |
| 2-124 | 4-Me | Et | |
| 2-125 | 2-Me, 4-Me | Et | |
| 2-126 | 3-Me, 5-Me | Et | |
| 2-127 | 2-OMe | Et | |
| 2-128 | 3-OMe | Et | |
| 2-129 | 4-OMe | Et | |
| 2-130 | 2-CF₃ | Et | |
| 2-131 | 3-CF₃ | Et | |
| 2-132 | 4-CF₃ | Et | |
| 2-133 | 3-CF₃, 5-CF₃ | Et | |
| 2-134 | 4-NO₂ | Et | |
| 2-135 | 2-F | Pr | |
| 2-136 | 3-F | Pr | |
| 2-137 | 2-Cl | Pr | |
| 2-138 | 2-F | iPr | |
| 2-139 | 3-F | iPr | |
| 2-140 | 2-Cl | iPr | |
| 2-141 | 2-F | Bu | |
| 2-142 | 3-F | Bu | |

TABLE 4-continued

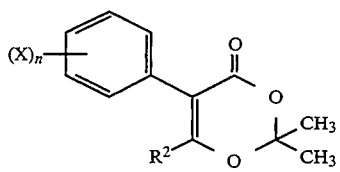

| Compound No. | X | R² | Melting Point [°C.] |
|---|---|---|---|
| 2-143 | 2-Cl | Bu | |
| 2-144 | 2-F | iBu | |
| 2-145 | 3-F | sBu | |
| 2-146 | 2-Cl | tBu | |
| 2-147 | 2-F | Hex | |
| 2-148 | 3-F | Hex | |
| 2-149 | 2-Cl | Hex | |

TABLE 7

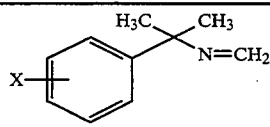

| Compound No. | X | Melting Point [°C.] |
|---|---|---|
| 3-1 | 2-F | |
| 3-2 | 3-F | 69.0–74.0 |
| 3-3 | 4-F | 155.5–160.5 |
| 3-4 | 2-Cl | Oily |
| 3-5 | 3-Cl | Oily |
| 3-6 | 4-Cl | 90.0–102.0 |
| 3-7 | 2-Br | |
| 3-8 | 3-Br | Oily |
| 3-9 | 4-Br | |
| 3-10 | 2-I | |
| 3-11 | 3-I | Oily |
| 3-12 | 4-I | |
| 3-13 | 2-F, 3-F | |
| 3-14 | 2-F, 4-F | |
| 3-15 | 2-F, 5-F | |
| 3-16 | 2-F, 6-F | |
| 3-17 | 3-F, 4-F | |
| 3-18 | 3-F, 5-F | |
| 3-19 | 2-F, 4-F, 6-F | |
| 3-20 | 2-F, 3-F, 4-F, 5-F, 6-F | |
| 3-21 | 2-Cl, 3-Cl | 89.5–94.0 |
| 3-22 | 2-Cl, 4-Cl | |
| 3-23 | 2-Cl, 5-Cl | |
| 3-24 | 2-Cl, 6-Cl | |
| 3-25 | 3-Cl, 4-Cl | 150.0–152.5 |
| 3-26 | 3-Cl, 5-Cl | 44.0–47.5 |
| 3-27 | 2-Cl, 4-Cl, 6-Cl | |
| 3-28 | 3-Cl, 4-Cl, 5-Cl | 159.5–161.5 |
| 3-29 | 2-Cl, 3-Cl, 4-Cl, 5-Cl, 6-Cl | |
| 3-30 | 2-Cl, 6-F | |
| 3-31 | 2-Me | |
| 3-32 | 3-Me | Oily |
| 3-33 | 4-Me | |
| 3-34 | 2-Me, 3-Me | |
| 3-35 | 3-Me, 4-Me | |
| 3-36 | 3-Me, 5-Me | 128.5–134.0 |
| 3-37 | 2-Me, 4-Me, 6-Me | |
| 3-38 | 3-Me, 4-Me, 5-Me | |
| 3-39 | 2-Me, 3-Me, 4-Me, 5-Me, 6-Me | |
| 3-40 | 3-Cl, 4-Me | Oily |
| 3-41 | 3-Cl, 4-Me, 5-Cl | |
| 3-42 | 2-Et | |
| 3-43 | 3-Et | |
| 3-44 | 4-Et | |
| 3-45 | 2-Pr | |
| 3-46 | 3-Pr | |
| 3-47 | 4-Pr | |
| 3-48 | 2-iPr | |
| 3-49 | 3-iPr | |
| 3-50 | 4-iPr | |

TABLE 7-continued

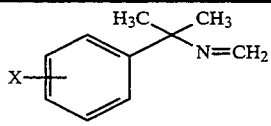

| Compound No. | X | Melting Point [°C.] |
|---|---|---|
| 3-51 | 2-Bu | |
| 3-52 | 3-Bu | |
| 3-53 | 4-Bu | |
| 3-54 | 2-iBu | |
| 3-55 | 3-sBu | |
| 3-56 | 4-tBu | |
| 3-57 | 3-Hex | |
| 3-58 | 2-OMe | |
| 3-59 | 3-OMe | Oily |
| 3-60 | 4-OMe | |
| 3-61 | 3-OMe, 4-OMe | |
| 3-62 | 3-OMe, 5-OMe | |
| 3-63 | 3-OMe, 4-OMe, 5-OMe | |
| 3-64 | 3-OMe, 4-Me | |
| 3-65 | 3-Cl, 4-OMe | Oily |
| 3-66 | 3-Br, 4-OMe | |
| 3-67 | 3-I, 4-OMe | |
| 3-68 | 3-Cl, 4-OMe, 5-Cl | 132.0–136.5 |
| 3-69 | 3-Br, 4-OMe, 4-Br | 102.5–108.0 |
| 3-70 | 2-OEt | |
| 3-71 | 3-OEt | |
| 3-72 | 4-OEt | |
| 3-73 | 2-OPr | |
| 3-74 | 3-OPr | |
| 3-75 | 4-OPr | |
| 3-76 | 2-OiPr | |
| 3-77 | 3-OiPr | |
| 3-78 | 4-OiPr | |
| 3-79 | 2-OBu | |
| 3-80 | 3-OBu | |
| 3-81 | 4-OBu | |
| 3-82 | 2-OiBu | |
| 3-83 | 3-OsBu | |
| 3-84 | 4-OtBu | |
| 3-85 | 2-OHex | |
| 3-86 | 3-OHex | |
| 3-87 | 4-OHex | |
| 3-88 | 2-CF₃ | |
| 3-89 | 3-CF₃ | Oily |
| 3-90 | 4-CF₃ | |
| 3-91 | 3-CF₃, 5-CF₃ | Oily |
| 3-92 | 2-CH₂CF₃ | |
| 3-93 | 2-CF₂CF₃ | |
| 3-94 | 2-OCHF₂ | |
| 3-95 | 3-OCHF₂ | Oily |
| 3-96 | 4-OCHF₂ | |
| 3-97 | 3-OCH₂CF₂CF₃ | |
| 3-98 | 3-OCH₂CH₂Cl | |
| 3-99 | 3-OCF₂CHCl₂ | |
| 3-100 | 3-OCF₂CHF₂ | |
| 3-101 | 3-OCF₂CH₂Cl | |

Next, production of the compounds of formula (I) and the intermediate compounds of formulae (II-1) and (III-1) will be described in more detail by examples.

EXAMPLE 1

Production of 5-(2-fluorophenyl)-2,2,6-trimethyl-2H,4H-1,3-dioxin-4-one (Compound No. 2-1)

A mixture of 2-(2-fluorophenyl)acetoacetic acid (5.1 g), acetone (4.2 ml), and acetic anhydride (5.4 ml) was kept at −20° C. and concentrated sulfuric acid (0.3 ml) was added thereto. This was kept at −15° C. and the reaction was carried out for 48 hours. The reaction mixture was added to an aqueous 10 % sodium carbonate solution (150 ml) which was ice-cooled, and the mixture was stirred for a short time at room temperature. White crystals which formed were collected by filtration, and washed well with water and then with hexane. The crystals obtained were dried well under reduced pressure to obtain the captioned compound (5.2 g).

EXAMPLE 2

Production of 5-(2-Chlorophenyl)2,2,6-trimethyl-2H,4H-1,3-dioxin-4-one (Compound No. 2-4)

A mixture of 2-(2-chlorophenyl)acetoacetic acid (9.6 g), acetone (6.8 ml), and acetic anhydride (8.8 ml) was kept at −15° and concentrated sulfuric acid (0.53 ml) was added thereto. This was kept at −15° C. and the reaction was carried out for 24 hours. The reaction mixture was added to an aqueous 10 % sodium carbonate solution (250 ml) which was ice-cooled, and the mixture was stirred for a short time at room temperature. White crystals which formed were collected by filtration, and washed well with water and then with hexane. The crystals obtained were dried well under reduced pressure to obtain the captioned compound (9.0 g).

Melting points of the substances produced according to Examples 1 and 2 and of substances produced by similar methods are shown in Table 6 above, and $^1$H-NMR peak values are shown in Table 8 below.

TABLE 8

| Compound No. | NMR δ [ppm.] (300 MHz) Solvent CDCl$_3$, TMS = 0 ppm |
|---|---|
| 2-1 | 1.79(s, 6H), 1.91(s, 3H), 7.06–7.21(m, 2H), 7.28–7.38(m, 2H) |
| 2-2 | 1.77(s, 6H), 1.96(s, 3H), 6.89–7.07(m, 3H), 7.28–7.39(m, 1H) |
| 2-3 | 1.77(s, 6H), 1.94(s, 3H), 7.04–7.12(m, 2H), 7.21–7.29(m, 2H) |
| 2-4 | 1.78(s, 3H), 1.86(s, 3H), 1.87(s, 3H), 7.22–7.48(m, 4H) |
| 2-5 | 1.77(s, 6H), 1.96(s, 3H), 7.14–7.35(m, 4H) |
| 2-6 | 1.77(s, 6H), 1.95(s, 3H), 7.21(d, 2H), 7.35(d, 2H) |
| 2-22 | 1.79(s, 3H), 1.81(s, 3H), 1.81(s, 3H), 2.24(s, 3H), 7.08–7.29(m, 4H) |
| 2-44 | 1.76(s, 3H), 1.83(s, 3H), 1.84(s, 3H), 3.80(s, 3H), 6.88–7.36(m, 4H) |
| 2-61 | 1.76(s, 3H), 1.77(s, 3H), 1.83(s, 3H), 7.28–7.34(m, 1H), 7.45–7.65(m, 2H), 7.71–7.78(m, 1H) |
| 2-62 | 1.79(s, 6H), 1.96(s, 3H), 7.36–7.62(m, 4H) |

EXAMPLE 3

Production of N-methylene-1-methyl-1-(3chlorophenyl)ethylamine (Compound No. 3-5)

1-Methyl-1-(3-chlorophenyl)ethylamine (5.0 g) was added slowly to formalin (aqueous 37% HCHO solution) (3.5 g) at room temperature. This was allowed to react as it was for 1 hour. A saturated aqueous sodium hydrogen carbonate solution was added to the reaction mixture, which was then extracted with ether. After it was washed with saturated saline, the organic layer was dried over anhydrous sodium sulfate. The solvent was distilled off under reduced pressure to obtain the captioned compound (5.6 g) as syrup.

EXAMPLE 4

Production of N-methylene-1-methyl-1-(3,5-dichlorophenyl)ethylamine (Compound No. 3-26)

1-Methyl-1-(3,5-dichlorophenyl)ethylamine (7.5 g) was added slowly to formalin (aqueous 37% HCHO solution) (4.6 g) at room temperature. This was allowed to react as it was for 7 hours. A saturated aqueous sodium hydrogen carbonate solution was added to the reaction mixture, which was then extracted with ether. After it was washed with saturated saline, the organic layer was dried over anhydrous sodium sulfate. The solvent was distilled off under reduced pressure to obtain the captioned compound (8.6 g) as white crystals.

Melting points of the substances produced according to Examples 3 and 4 and of substances produced by similar methods are shown in Table 7 above, and $^1$H-NMR peak values are shown in Table 9 below.

TABLE 9

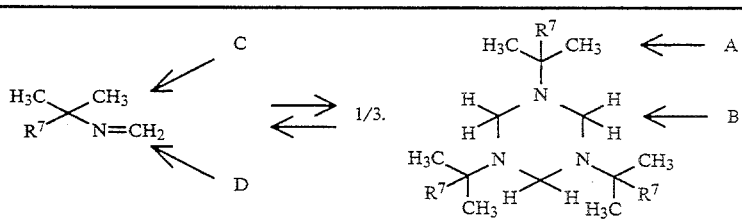

| Compound No. | NMR δ[ppm.] (300 MHz) Solvent CDCl$_3$, TMS = 0 ppm |
|---|---|
| 3-2 | 1.36(s, A), 3.49(brs, B), 6.67–6.86(m, 1H), 7.10–7.32(m, 3H) |
| 3-3 | 1.33(s, A), 1.54(s, C), 3.46(brs, B), 6.86–7.46(m, 4H+D) |
| 3-4 | 1.68(s, C), 7.0–7.7(m, 4H+D) |
| 3-5 | 1.35(s, A), 1.51(s, C), 3.48(brs, B), 7.08–7.52(m, 4H+D) |
| 3-6 | 1.33(s, A), 1.53(s, C), 3.46(brs, B), 7.2–7.5(m, 4H+D) |
| 3-11 | 1.65(s, C), 6.98–7.83(m, 4H+D) |
| 3-21 | 1.69(s, C), 7.0–7.7(m, 4H+D) |
| 3-25 | 1.34(s, A), 1.52(s, C), 3.46(brs, B), 7.18–7.52(m, 3H+D) |
| 3-26 | 1.33(s, A), 1.51(s, C), 3.46(brs, B), 7.18–7.38(m, 3H), 7.42 and 7.47(ABq, D) |

TABLE 9-continued

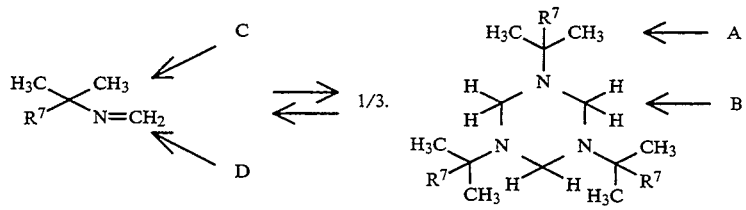

| Compound No. | NMR δ[ppm.] (300 MHz) Solvent CDCl$_3$, TMS = 0 ppm |
|---|---|
| 3-32 | 1.33(s, A), 1.67(s, C), 2.33 and 2.34(a pair of s, 3H), 3.48(brs, B), 6.93–7.40(m, 4H+D) |
| 3-36 | 1.31(s, A), 1.54(s, C), 2.31(s, 6H), 3.47(brs, B), 6.78–7.18(m, 3H), 7.35 and 7.41(ABq, D) |
| 3-59 | 1.35(s, A), 1.55(s, C), 3.50(brs, B), 3.81(S, 3H), 6.64–7.46(m, 4H), 7.34 and 7.46(ABq, D) |
| 3-68 | 1.32(s, A), 1.51(s, C), 3.48(brs, B), 3.87 and 3.89(a pair of s, 2H), 7.29 and 7.38(a pair of s, 2H), 7.40 and 7.47 (ABq, D) |
| 3-69 | 1.31(s, A), 1.50(s, C), 3.49(brs, B), 3.86 and 3.87(a pair of s, 2H), 7.34 and 7.46(ABq, D), 7.50 and 7.62 (a pair s, 2H) |
| 3-89 | 1.36(s, A), 1.57(s, C), 3.49(brs, B), 7.29–7.75(m, 4H+D) |
| 3-91 | 1.35(s, A), 1.57(s, C), 3.54(brs, B), 7.10–8.03(m, 3H+D) |
| 3-95 | 1.35(s, A), 1.55(s, C), 3.48(brs, B), 6.49 and 6.51(a pair of t, 2H), 6.85–7.35(m, 4H), 7.41(Abq, D) |

EXAMPLE 5

Production of 6-methyl-3-[1-methyl-1-(3,5-dichlorophenyl)ethyl]-5-phenyl-2,3-dihydro-4H-1,3-oxazin-4-one (Compound No. 248)

A mixture of 5-phenyl-2,2,6-trimethyl-2H,4H-1,3-dioxin-4-one (0.65 g) and N-methylene-1-methyl-1-(3,5-dichlorophenyl)ethyl amine (compound of Example 4) (0.65 g) was heated at 150° C. for 30 minutes for reaction. The reaction mixture was recrystallized from a mixed solvent composed of hexane and ethyl acetate to obtain the captioned compound (0.90 g).

EXAMPLE 6

Production of 6-methyl-3-[1-methyl-1-(3-chlorophenyl)ethyl]-5-phenyl-2,3-dihydro-4H-1,3-oxazin-4-one (Compound No. 73)

A mixture of 5-phenyl-2,2,6-trimethyl-2H,4H-1,3-dioxin-4-one (1.0 g) and N-methylene-1-methyl-1-(3-chlorophenyl)ethylamine (Compound of Example 3) (0.76 g) was heated at 15 0° C. for 30 minutes for reaction. The reaction mixture was purified by silica gel chromatography to obtain the captioned compound (1.0 g).

EXAMPLE 7

Production of 5-(2-fluorophenyl)-6-methyl-3-[1-methyl-1-(3-chlorophenyl)ethyl]-2,3-dihydro-4H-1,3-oxazin-4-one (Compound No. 74)

Xylene (2 ml ) was added to a mixture of 5-(2-fluorophenyl)-2,2 ,6-trimethyl-2H,4H-1,3-dioxin-4-one (compound of Example 1 ) (0.71 g) and N-methylene-1-methyl1-(3-chlorophenyl)ethylamine (compound of Example 3) (0.6 g), and the resulting mixture was heated at reflux for 20 minutes for reaction. The reaction mixture was purified by silica gel chromatography to obtain the captioned compound (0.9 g).

EXAMPLE 8

Production of 6-methyl-3-(1-methyl-1-phenylethyl) -5-phenyl-2,3-dihydro-4H-1,3-oxazin-4-one (Compound No. 1)

5-Phenyl-2,2,6-trimethyl-2H,4H-1,3-dioxin-4-one (2.2 g) and N-methylene-1-methyl-1-phenylethylamine (1.7 g) were reacted at 155° C. for 20 minutes. The reaction mixture was recrystallized from hexane and ether solvent to obtain the captioned compound (1.6 g). Example 9 Production of 3-(1-methyl-1-phenylethyl)-5-phenyl-2,3-dihydro-4H -1,3-oxazin-4-one (Compound No. 388)

Xylene (2 ml) was added to a mixture of 5-phenyl-2,2-dimethyl-2H,4H-1,3-dioxin-4-one (0.82 g) and N-methylene-1-methyl-1-phenylethylamine (0.59 g), and the resulting mixture was heated at reflux for 20 minutes for reaction. The reaction mixture was purified by silica gel chromatography to obtain the captioned compound (0.9 g).

EXAMPLE 10

Production of 6-ethyl-3-(1-methyl-1-phenylethyl)-5-phenyl-2,3-dihydro-4H-1,3-oxazin-4-one (Compound No. 402)

Xylene (2 ml) was added to a mixture of 6-ethyl-5-phenyl-2,2-dimethyl-2H,4H-1,3-dioxin-4-one (0.70 g) and N-methylene-1-methyl-1-phenylethylamine (0.44 g), and the resulting mixture was heated at reflux for 20 minutes for reaction. The reaction mixture was purified by silica gel chromatography to obtain the captioned compound (0.72 g).

EXAMPLE 11

Production of 5-isobutyl-6-methyl-3-[1-methyl-1-(3-chlorophenyl)ethyl]-2,3-dihydro-4H-1,3-oxazin -4-one (Compound No. 514)

Xylene (1 ml) was added to a mixture of 5-isobutyl-2,2,6-trimethyl-2H,4H-1,3-dioxin-4-one (0.59 g) and N-methylene-1-methyl-1-(3-chlorophenyl)ethylamine (0.55 g), and the resulting mixture was heated at reflux for 60 minutes for reaction. The reaction mixture was purified by silica gel chromatography to obtain the captioned compound (0.52 g).

EXAMPLE 12

Production of 6-methyl-3-[1-methyl-1-(3chlorophenyl)propyl]-2,3-dihydro-4H-1,3-oxazin-4-one (Compound No. 801)

A mixture of 5-phenyl-2,2,6-trimethyl-2H,4H-1,3-dioxin-4-one (0.65 g) and N-methylene-1-methyl-1-(3- chlorophenyl)propylamine (0.76 g) was heated at 150° C. for 30 minutes for reaction. The reaction mixture was purified by silica gel chromatography to obtain the captioned compound (0.79 g).

EXAMPLE 13

Production of 3-[1-(3-chlorophenyl)cyclopentyl]-6-methyl-5-phenyl-2,3-dihydro-4H-1,3-oxazin-4-one (Compound No. 857)

A mixture of 5-phenyl-2,2,6-trimethyl-2H,4H-1,3-dioxin-4-one (0.65 g) and N-methylene-1-(3-chlorophenyl)cyclopentylamine (0.78 g) and xylene (3 ml) was heated at reflux for 30 minutes for reaction. The reaction mixture was purified by silica gel chromatography to obtain the captioned compound (0.97 g).

EXAMPLE 14

Production of 6-methyl-5-phenyl-3-(1,1,2,2-tetramethylpropyl)-2,3-dihydro-4H-1,3-oxazin-4-one (Compound No. 666)

A mixture of 5-phenyl-2,2,6-trimethyl-2h,4h-1,3-dioxin-4-one (0.65 g), N-methylene-1,1,2,2-tetramethylpropylamine (0.54 g) and xylene (2 ml) was heated at reflux for 30 minutes for reaction. The reaction mixture was purified by silica gel chromatography to obtain the captioned compound (0.40 g).

EXAMPLE 15

Production of 3-(1,1-dimethyl-2-phenylethyl)6-methyl-5-phenyl-2,3-dihydro-4H-1,3-oxazin-4-one (Compound No. 700)

5-phenyl-2,2,6-trimethyl-2H,4H-1,3-dioxin-4-one (0.65 g) and N-methylene-1,1-dimethyl-2-phenylethylamine (0.63 g) were reacted at 140° for 30 minutes. The reaction mixture was purified by silica gel chromatography to obtain the captioned compound (0.74 g).

EXAMPLE 16

Production of 6-methyl-3-[1-methyl-1-(2naphthyl)ethyl]-5-phenyl-2,3-dihydro-4H-1,3-oxazin-4-one (Compound No. 606)

A mixture of 5-phenyl-2,2,6-trimethyl-2H,4H-1,3-dioxin-4-one (0.65 g), N-methylene-1-methyl-1-(2-naphthyl)ethylamine (0.60 g) and xylene (3 ml) was heated at reflux for 20 minutes for reaction. The reaction mixture was purified by silica gel chromatography to obtain the captioned compound (0.40 g).

Melting points of the substances produced according to Examples 5 to 16 and of substances produced by similar methods are shown in Tables 1 to 6 above, and $^1$H-NMR peak values are shown in Table 10 below.

TABLE 10

| Compound No. | NMR δ [ppm.] (300 MHz) Solvent CDCl$_3$, TMS = 0 ppm |
|---|---|
| 1 | 1.82(s, 6H), 1.89(s, 3H), 5.07(s, 2H), 7.21–7.45(m, 10H) |
| 2 | 1.82(s, 6H), 1.88(s, 3H), 5.10(s, 2H), 7.0–7.2(m, 2H), 7.2–7.5(m, 7H) |
| 3 | 1.76(s, 6H), 1.90(s, 3H), 5.22(s, 2H), 7.15–7.35(m, 5H), 7.37–7.49(m, 2H), 7.54–7.62(m, 2H) |
| 4 | 1.80(s, 3H), 1.81(s, 3H), 1.88(s, 3H), 5.07(s, 2H), 6.97–7.05(m, 2H) 7.20–7.43(m, 7H) |
| 5 | 1.82(s, 3H), 1.83(s, 6H), 5.12 and 5.14(ABq, 2H), 7.18–7.45(m, 9H) |
| 6 | 1.82(s, 6H), 1.90(s, 3H), 5.08(s, 2H), 7.11–7.44(m, 9H) |
| 7 | 1.81(s, 6H), 1.89(s, 3H), 5.07(s, 2H), 7.18–7.42(m, 9H) |
| 23 | 1.78(s, 3H), 1.79(s, 3H), 1.83(s, 3H), 2.14(s, 3H) 5.11 and 5.13(ABq, 2H), 7.08–7.44(m, 9H) |
| 45 | 1.81(s, 6H), 1.82(s, 3H), 3.75(s, 3H), 5.10(s, 2H) 6.85–6.96(m, 2H), 7.16–7.45(m, 7H) |
| 62 | 1.73(s, 3H), 1.79(s, 3H), 1.83(s, 3H), 5.09(s, 2H), 7.19–7.27(m, 1H) 7.27–7.43(m, 4H), 7.52(t, 1H), 7.66(d, 1H) |
| 63 | 183(s, 6H), 1.89(s, 3H), 5.10(s, 2H), 7.20–7.62(m, 9H) |
| 73 | 1.77(s, 6H), 1.91(s, 3H), 5.18(s, 2H), 7.10–7.42(m, 9H) |
| 74 | 1.76(s, 6H), 1.89(s, 3H), 5.20(s, 2H), 7.00–7.13(m, 2H). 7.17–7.32(m, 5H), 7.33–7.37(m, 1H) |
| 75 | 1.77(s, 6H), 1.92(s, 3H), 5.18(s, 2H), 6.91–7.07(m, 3H), 7.17–7.37(m, 5H) |
| 76 | 1.76(s, 6H), 1.90(s, 3H), 5.18(s, 2H), 6.96–7.10(m, 3H) 7.17–7.35(m, 5H) |
| 77 | 1.77(s, 6H), 1.86(s, 3H), 5.24 and 5.25(ABq, 2H), 7.17–7.42(m, 8H) |
| 78 | 1.77(s, 6H), 1.92(s, 3H), 5.18(s, 2H), 7.1–7.4(m, 8H) |
| 79 | 1.76(s, 6H), 1.90(s, 3H), 5.28(s, 2H), 7.15–7.37(m, 8H) |
| 104 | 1.73(s, 3H), 1.79(s, 3H), 1.81(s, 3H), 2.12(s, 3H), 5.23 and 5.25(ABq, 2H), 7.04–7.38(m, 8H) |
| 135 | 1.75(brs, 6H), 1.85(s, 3H), 3.74(s, 3H), 5.21(s, 2H), 6.86(d, 1H), 6.91(t, 1H), 7.12–7.30(m, 5H), 7.34–7.38(m, 1H) |
| 161 | 1.75(s, 3H), 1.76(s, 3H), 1.77(s, 3H), 5.23 and 5.25(ABq, 2H), 7.18–7.32(m, 4H), 7.33(s, 1H), 7.39(t, 1H), 7.52(t, 1H), 7.66(d, 1H) |
| 162 | 1.78(s, 6H), 1.91(s, 3H), 5.20(s, 2H), 7.14–7.62(m, 8H) |
| 176 | 1.78(s, 6H), 1.91(s, 3H), 5.17(s, 2H), 6.88–6.96(m, 1H), 7.06–7.13(m, 1H), 7.17(d, 1H), 97.21–7.36(m, 6H) |
| 177 | 1.78(s, 6H), 1.89(s, 3H), 5.19(s, 2H), 6.87–6.96(m, 1H), 7.00–7.14(m, 3H), 7.17(d, 1H), 7.21–7.34(m, 3H) |
| 180 | 1.77(s, 3H), 1.79(s, 3H), 1.85(s, 3H), 5.21 and 5.24(ABq, 2H), 6.87–7.43(m, 8H) |
| 187 | 1.75(s, 3H), 1.79(s, 3H), 1.80(s, 3H), 2.12(s, 3H) 5.22 and 5.22(ABq, 2H), 6.86–7.35(m, 8H) |
| 208 | 1.75(s, 3H), 1.76(s, 3H), 1.79(s, 3H), 5.18 and 5.22(ABq, 2H), 6.87–6.95(m, 1H), 7.07(dt, 1H), 7.14(d, 1H), 7.24–7.33(m, 2H), 7.39(t, 1H), 7.52(t, 1H), 7.66(d, 1H) |
| 217 | 1.80(s, 6H), 1.90(s, 3H), 5.12(s, 2H), 6.96–7.42(m, 9H) |

TABLE 10-continued

| Compound No. | NMR δ [ppm.] (300 MHz) Solvent CDCl₃, TMS = 0 ppm |
|---|---|
| 221 | 1.86(s, 6H), 1.87(s, 3H), 5.33(s, 2H), 7.08–7.14(m, 1H), 7.17–7.31(m, 7H), 7.46–7.50(m, 1H) |
| 225 | 1.75(s, 6H), 1.89(s, 3H), 5.14(s, 2H), 7.19–7.35(m, 9H) |
| 230 | 1.77(s, 6H), 1.92(s, 3H), 5.18(s, 2H), 7.17–7.41(m, 8H), 7.51(t, 1H) |
| 232 | 1.76(s, 6H), 1.89(s, 3H), 5.20(s, 2H), 6.98–7.14(m, 2H), 7.15–7.38(m, 2H), 7.50(t, 1H) |
| 233 | 1.76(s, 6H), 1.91(s, 3H), 5.17(s, 2H), 7.06(t, 1H), 7.14–7.40(m, 6H), 7.56(brd, 1H), 7.70(t, 1H) |
| 235 | 1.73(s, 6H), 1.93(s, 3H), 3.87(s, 3H), 5.25(s, 2H), 7.20–7.32(m, 5H), 7.47(s, 2H) |
| 236 | 1.73(s, 6H), 1.92(s, 3H), 3.87(s, 3H), 5.28(s, 2H), 7.01–7.31(m, 4H), 7.47(s, 2H) |
| 243 | 1.85(s, 6H), 1.88(s, 3H), 5.39(s, 2H), 7.11–7.45(m, 8H) |
| 247 | 1.74(s, 6H), 1.92(s, 3H), 5.24(s, 2H), 7.18–7.45(m, 8H) |
| 248 | 1.73(s, 6H), 1.93(s, 3H), 5.26(s, 2H), 7.19–7.35(m, 8H) |
| 249 | 1.71(s, 3H), 1.73(s, 3H), 1.88(s, 3H), 5.33 and 5.34(ABq, 2H), 7.17–7.42(m, 7H) |
| 252 | 1.66(s, 3H), 1.74(s, 3H), 1.82(s, 3H), 2.10(s, 3H), 5.30 and 5.32(ABq, 2H), 7.01–7.26(m, 7H) |
| 253 | 1.73(s, 6H), 1.92(s, 3H), 5.29(s, 2H), 7.00–7.32(m, 7H) |
| 256 | 1.72(s, 6H), 1.94(s, 3H), 5.30(s, 2H), 7.18–7.35(m, 5H), 7.35(s, 2H) |
| 257 | 1.72(s, 6H), 1.93(s, 3H), 5.33(s, 2H), 7.00–7.14(m, 2H), 7.22–7.30(m, 2H), 7.35(s, 2H) |
| 263 | 1.81(s, 6H), 1.88(s, 3H), 2.36(s, 3H), 5.04(s, 2H), 6.95–7.40(m, 9H) |
| 267 | 1.81(s, 6H), 1.83(s, 3H), 2.36(s, 3H), 5.11 and 5.13(ABq, 2H), 7.02–7.43(n, 8H) |
| 274 | 1.78(s, 3H), 1.78(s, 3H), 1.82(s, 3H), 2.15(s, 3H), 2.35(s, 3H), 5.11 and 5.12(ABq, 2H), 7.01–7.28(m, 8H) |
| 283 | 1.82(s, 6H), 1.89(s, 3H), 2.37(s, 3H), 5.08(s, 2H), 7.04–7.61(m, 8H) |
| 290 | 1.77(s, 6H), 1.90(s, 3H), 2.34(s, 3H), 5.14(s, 2H), 7.15–7.37(m, 8H) |
| 296 | 1.80(s, 6H), 1.89(s, 3H), 2.32(s, 6H), 5.03(s, 2H), 6.86–7.36(m, 8H) |
| 321 | 1.73(s, 6H), 1.93(s, 3H), 3.88(s, 3H), 5.25(s, 2H), 7.27(s, 2H), 7.20–7.36(m, 5H) |
| 322 | 1.73(s, 6H), 1.92(s, 3H), 3.88(s, 3H), 5.28(s, 2H), 7.27(s, 2H), 7.01–7.14(m, 2H), 7.22–7.31(m, 2H) |
| 323 | 1.81(s, 6H), 1.89(s, 3H), 3.80(s, 3H), 5.01(s, 2H), 6.74–7.36(m, 9H) |
| 324 | 1.80(s, 6H), 1.87(s, 3H), 3.80(s, 3H), 5.10(s, 2H), 6.74–7.37(m, 8H) |
| 325 | 1.80(s, 3H), 1.81(s, 3H), 1.83(s, 3H), 3.80(s, 3H), 5.10 and 5.14(ABq, 2H), 6.74–7.36(m, 8H) |
| 358 | 11.81(s, 6H), 1.89(s, 3H), 5.08(s, 2H), 6.90–7.05(m, 3H), 7.20–7.43(m, 6H) |
| 359 | 1.77(s, 6H), 1.89(s, 3H), 5.26(s, 2H), 6.97–7.11(m, 2H), 7.18–7.28(m, 2H), 7.38–7.40, (m, 2H), 7.54–7.62(m, 2H) |
| 360 | 1.79(s, 6H), 1.86(s, 3H), 5.31 and 5.31(ABq, 2H), 7.16–7.64(m, 8H) |
| 363 | 1.73(s, 3H), 1.81(s, 3H), 1.81(s, 3H), 2.06(s, 3H), 5.29 and 5.32(ABq, 2H), 7.00–7.62(m, 8H) |
| 365 | 1.82(s, 6H), 1.91(s, 3H), 5.55(s, 2H), 7.15–7.76(m, 8H) |
| 370 | 1.78(s, 6H), 1.94(s, 3H), 5.37(s, 2H), 7.12–7.18(m, 2H), 7.20–7.35(m, 3H), 7.72(brs, 1H), 7.77(brs, 2H) |
| 374 | 1.78(s, 6H), 1.91(s, 3H), 5.20(s, 2H), 6.50(t, 1H), 6.94–6.99(m, 1H), 7.11–7.14(m, 1H), 7.19–7.36(m, 7H) |
| 375 | 1.76(s, 6H), 1.89(s, 3H), 5.22(s, 2H), 6.49(t, 1H), 6.93–7.38(m, 8H) |
| 376 | 1.77(s, 3H), 1.78(s, 3H), 1.86(s, 3H), 5.258 and 5.26(ABq, 2H), 6.50(t, 1H), 6.93–6.99(m, 1H), 7.11–7.14(m, 1H), 7.19–7.42(m, 6H) |
| 388 | 1.84(s, 6H), 5.14(s, 2H), 7.21–7.46(m, 11H) |
| 392 | 1.79(s, 6H), 5.24(s, 2H), 7.17–7.45(m, 10H) |
| 402 | 1.06(t, 3H), 1.82(s, 6H), 2.17(q, 2H), 5.08(s, 2H) 7.21–7.44(m, 10H) |
| 403 | 1.08(t, 3H), 1.77(s, 6H), 2.19(q, 2H), 5.18(s, 2H), 7.17–7.36(m, 9H) |
| 418 | 1.10(t, 3H), 1.73(s, 6H), 2.21(q, 2H), 3.87(s, 3H), 5.26(s, 2H), 7.18–7.36(m,5H), 7.46(s, 2H) |
| 421 | 0.85(t, 3H), 1.45–1.61(m, 2H), 1.82(s, 6H), 2.14(t, 2H), 5.07(s, 2H), 7.18–7.45(m, 10H) |
| 422 | 0.86(t, 3H), 1.45–1.63(m, 2H), 1.77(s, 6H), 2.16(t, 2H), 5.18(s, 2H), 7.10–7.40(m, 9H) |
| 440 | 1.05(d, 6H), 1.82(s, 6H), 2.50–2.65(m, 1H), 5.07(s, 2H), 7.15–7.45(m, 10H) |
| 505 | 0.86(d, 6H), 1.61–1.76(m, 1H), 1.77(s, 6H), 1.96(s, 3H), 2.12(d, 2H), 4.96(s, 2H), 7.18–7.39(m, 5H) |
| 514 | 0.85(d, 6H), 1.59–1.70(m, 1H), 1.71(s, 6H), 1.98(s, 3H), 2.10(d, 2H), 5.05(s, 2H), 7.15–7.31(m, 4H) |
| 606 | 1.90(s, 3H), 1.93(s, 6H), 5.07(s, 2H), 7.21–7.36(m, 5H), 7.42–7.52(m, 2H), 7.61(dd, 1H), 7.78–7.88(m, 4H) |
| 666 | 0.98(s, 9H), 1.56(s, 6H), 1.86(s, 3H), 5.20(s, 2H), 7.20–7.42(m, 5H) |
| 700 | 1.51(s, 6H), 1.82(s, 3H), 3.21(s, 2H), 4.66(s, 2H), 7.10–7.45(m, 10H) |
| 704 | 1.53(s, 6H), 1.86(s, 3H), 3.45(s, 2H), 4.86(s, 2H), |

TABLE 10-continued

| Compound No. | NMR δ [ppm.] (300 MHz) Solvent CDCl₃, TMS = 0 ppm |
|---|---|
|  | 7.10–7.45(m, 9H) |
| 705 | 1.50(s, 6H), 1.84(s, 3H), 3.20(s, 2H), 4.73(s, 2H), 6.99–7.44(m, 9H) |
| 706 | 1.49(s, 6H), 1.81(s, 3H), 3.19(s, 2H), 4.68(s, 2H), 6.83–7.42(m, 9H) |
| 710 | 1.51(s, 6H), 1.88(s, 3H), 2.18–2.28(m, 2H), 2.52–2.68(m, 2H), 5.18(s, 2H), 7.12–7.42(m, 10H) |
| 801 | 0.89(t, 3H), 1.65(s, 3H), 1.93(s, 3H), 1.95–2.10(m, 1H), 2.48–2.63(m, 1H), 5.18 and 5.22(ABq, 2H), 7.15–7.38(m, 9H) |
| 818 | 1.49(s, 3H), 1.56(s, 9H, 1.79(s, 3H), 4.35(s, 2H), 7.20–7.50(m, 10H) |
| 857 | 1.60–1.75(m, 2H), 1.75–1.88(m, 2H), 1.89(s, 3H), 2.30–2.53(m, 4H), 5.22(s, 2H), 7.15–7.40(m, 9H) |
| 860 | 1.30–1.90(m, 10H), 1.92(s, 3H), 5.23(s, 2H), 7.13–7.40(m, 9H) |
| 330 | 1.78(s, 6H), 1.90(s, 3H), 3.89(s, 3H), 5.12(s, 2H), 6.86–7.42(m, 8H) |
| 567 | 1.72(s, 6H), 2.25(s, 3H), 3.21(s, 1H), 5.15(s, 2H), 7.17–7.23(m, 3H) |

The compounds of formula (I) provided by this invention have strong herbicidal activities against many kinds of weeds and very weak phytotoxicities to useful crops as will be apparent from test examples described later on.

For example, the compounds of this invention exhibit excellent herbicidal effects at very low doses over a wide time range of from germination to and including growth period of annual weeds such as *Echinochloa crus-galli* P. Beauv., *Cyperus difformis* L., *Monochoria vaginalis* Presl., *Rotala indica* Koehne, *Lindernia procumbens* Philcox, and *Dopatrium junceum* Hamilt., and perennial weeds such as *Scirpus hotarui* Ohwi, *Eleocharis acicularis* Roem. et Schult. var. *longiseta* Svenson, *Alisma canaliculatum* A. Br. et Bouché and *Cyperus serotinus* Rottb., while simultaneously showing high safety toward paddy field rice plant. The compounds of this invention are featured that when applied to soil or stems and leaves, they exhibit high herbicidal effects on various weeds which cause problems also in farmlands perennial and annual Cyperaceous weeds such as *Cyperus rotundus* L., *Cyperus polystachyos* Rottb.*, *Cyperus brevifolius* Hassk. var. *leiolepis* T. Koyama, *Cyperus microiria* Steud., and *Cyperus iria* L.*, and Gramineous weeds such as *Echinochloa crus-galli* P. Beauv., *Digitaria adscendens* Henr., *Setaria viridis* P. Beauv., *Poa annua* L., *Sorghum halepense* Pers, and *Alopecurus aequalis* Sobol. var. *amurensis* Ohwi as well as broad-leaved weeds such as, for example, *Polygonum hydropiper* L., *Amaranthus retroflexus* L., and *Chenopodium album* L., while simultaneously showing high safety toward soybean, cotton, sugar beet, upland rice plant, wheat, etc.

Further, the compounds of this invention can be used not only in paddy fields, and uplands, but also in orchards, mulberry fields, lawn, and non-crop lands.

The compounds of this invention can be used in combination with other agricultural and horticultural active compounds. For example, when the compounds of this invention are used in combination with other compounds having herbicidal or growth controlling activities, they ekhibit complete herbicidal effects on weeds which are difficult to control with each of the compounds applied singly, and effectively control various weeds by synergistic herbicidal effects at doses at which a single compound is not effective, and they are highly safe toward paddy field rice plant, soybean, cotton, sugar beet, upland rice plant, wheat, etc., so that they can provide herbicides which are very useful in agriculture.

Thus, according to this invention, there are provided herbicides containing 1,3-oxazin-4-one derivatives represented by formula (I) above as active ingredients.

When the compounds of this invention are used as herbicides, they are mixed with agriculturally or horticulturally acceptable carriers or diluents and formed into various formulations, for example, dusts, granules, wettable powders, emulsifiable concentrates, soluble powders, flowables, etc. They can be used as mixtures or in combination with other agricultural chemicals, for example, fungicides, insecticides, acaricides, herbicides, plant growth regulators, fertilizers and soil.

In particular, the use of the compounds of this invention as mixtures with other herbicides can lead not only to reduction in dose and reduction in manpower, but also to broadening of herbicidal spectrum attributable to cooperative activities and further improved effects attributable to synergistic activities by the both agents.

The carriers or diluents used upon formulation include generally used solid or liquid carriers or diluents.

Examples of the solid carriers or diluents include clays represented by kaolinites, montmorillonites, illites, polygroskites, etc., more specifically pyrophyllite, attapulgite, sepiolite, kaolinite, bentonite, vermiculite, mica, talc, etc.; and other inorganic substances such as gypsum, calcium carbonate, dolomite, diatomaceus earth, magnesium line, phosphorus lime, zeolite, silicic anhydride, synthetic calcium silicate, etc.; organic substances of vegetable origin such as soybean flour, tobacco flour, walnut flour, wheat flour, wood flour, starch, crystalline cellulose, etc.; synthetic or natural polymers such as coumarone resin, petroleum resin, alkyd resin, polyvinyl chloride, polyalkylene glycol, ketone resin, ester gum, copal gum, dammar gum, etc.; waxes such as carnauba wax, bee wax, etc.; or urea and the like.

Examples of suitable liquid carriers or diluents include paraffin or naphthene hydrocarbons such as kerosene, mineral oil, spindle oil, white oil, etc.; aromatic hydrocarbons such as xylene, ethylbenzene, cumene, methylnaphthalene, etc.; chlorinated hydrocarbons such as trichloroethylene, monochlorobenzene, o-chlorotoluene, etc.; ethers such as dioxane, tetrahydrofuran, etc., ketones such as acetone, methyl ethyl ketone, diisobutyl ketone, cyclohexanone, acetophenone, isophorone; esters such as ethyl acetate, amyl acetate, ethylene glycol acetate, diethylene glycol acetate, dibutyl maleate, diethyl succinate, etc.; alcohols such as methanol, n-hexanol, ethylene glycol, diethylene glycol, cyclohexanol, benzyl alcohol, etc.; ether alcohols such as ethylene glycol ethyl ether, diethylene glycol butyl ether, etc.; polar solvents such as dimethylformamide, dimethyl sulfoxide, etc., or water.

In addition, surfactants and other auxiliary agents may be used for various purposes such as emulsification, dispersion, humidification, spreading, dilation, combination destruction control, stabilization of active ingredients, improvement of flowability, prevention of corrosion, prevention of freezing, etc., of the compounds of this invention.

As the surfactant, there may be used one of any type among nonionic, anionic, cationic and amphoteric surfactants. Usually, nonionic and (or) anionic surfactants are used. Examples of suitable nonionic surfactants include addition polymerization products of ethylene oxide with higher alcohols such as lauryl alcohol, stearyl alcohol, oleyl alcohol, etc.; addition polymerization products of ethylene oxide with alkylnaphthols such as butylnaphthol, octylnaphthol, etc.; addition polymerization products of ethylene oxide with higher fatty acids such as palmitic acid, stearic acid, oleic acid, etc.; higher fatty acid esters of polyhydric alcohols such as sorbitan, and addition polymerization products of ethylene oxide therewith; etc.

As suitable anionic surfactants, there can be cited, for example, alkyl sulfate salts such as sodium laurylsulfate, amine salts of sulfuric acid ester of oleyl alcohol, etc., alkyl sulfonate salts such as sodium dioctyl sulfosuccinate, sodium 2-ethylhexenesulfonate, etc., arylsulfonate salts such as sodium isopropyl naphthalenesulfonate, sodium methylenebisnaphthalenesulfonate, sodium lignin sulfonate, sodium dodecyl benzenesulfonate, etc., and the like.

Further, for the purpose of improvement of properties of formulations, enhancement of effects, etc., the herbicides of this invention may be used in combination with polymers and other auxiliary agents such as casein, gelatin, albumin, glue, sodium alginate, carboxymethylcellulose, methylcellulose, hydroxyethylcellulose, polyvinyl alcohol, etc.

The above-described carriers or diluents and various auxiliary agents are used singly or in combination with others depending on the purpose taking into consideration forms of formulation, conditions of application, etc.

The contents of active ingredients in the various formulations of this invention thus prepared may vary widely depending on forms of formulation, and suitable content is within the range of usually 0.1 to 99% by weight, and preferably 1 to 80% by weight, which is most suitable.

Wettable powders contain active ingredient compounds in amounts of usually 25 to 90%, and the remainder solid carriers or diluents and dispersion wetting agents. If necessary, colloid proltection agents, defoaming agents, etc. may be added thereto.

Granules contain, for example, active ingredient compounds in amounts of usually 1 to 35%, and the remainder may be solid carriers or diluents and surfactants. The active ingredient compounds may be mixed with solid carriers or diluents uniformly, or fixed to or adsorbed on the surfaces of solid carriers or diluents uniformly. It is preferred that the diameter of the granules be within the range of about 0.2 to 1.5 mm.

Emulsifiable concentrates contain, for example, active ingredient compounds of usually 5 to 30%, and in addition about 5 to 20% by weight of emulsifiers, the remainder being liquid carriers or diluents. If necessary, spreading agents and anticorrosive agents may be added thereto.

Flowables contain, for example, active ingredient compounds in amounts of usually 5 to 50%, and in addition 3 to 10% by weight of dispersion wetting agents, and the remainder being water. If necessary, protective colloid agents, preservatives, defoaming agents, etc. may be added thereto.

The compounds of this invention may be used as herbicides as they are or in any of the forms of formulation described above.

The herbicides of this invention may be applied in effective amounts to various places to be protected, for example, farm-lands such as paddy fields and upland, or non-crop lands, prior to germination of weeds or to weeds of various stages from after germination to growth period. The dose is generally, as amount of active ingredients, on the order of 0.1 to 10,000 g/ha, preferably 1 to 5,000 g/ha. The dose may be varied properly depending on the kind of objective weeds, their growth stages, places of application, weather, etc.

Next, several embodiments of formulations using the compounds of this invention. In the following formulations, all "parts" are by weight.

| Formulation Example 1 (Emulsifiable concentrate) | |
|---|---|
| Compound No. 73 | 20 parts |
| Xylene | 50 parts |
| Cyclohexanone | 20 parts |
| Calcium dodecylbenzenesulfonate | 5 parts |
| Polyoxyethylenestyryl phenyl ether | 5 parts |

The above substances were mixed and dissolved uniformly to obtain 100 parts of an emulsifiable concentrate.

| Formulation Example 2 (Wettable powder) | |
|---|---|
| Compound No. 73 | 20 parts |
| Clay | 70 parts |
| Calcium ligninsulfonate | 7 parts |
| Condensate of alkylnaphthalene-sulfonic acid with formaldehyde | 5 parts |

The above substances were mixed and pulverized using a jet mill mixed to obtain 100 parts of a wettable powder.

| Formulation Example 3 (Flowable) | |
|---|---|
| Compound No. 74 | 20 parts |
| Sodium di(2-ethylhexyl sulfosuccinate | 2 parts |
| Polyoxyethylene nonylphenyl ether | 2 parts |
| Defoaming agent | 0.5 part |
| Propylene glycol | 5 parts |
| Water | 70.5 parts |

The above substances were mixed and pulverized using a wet ball mill to obtain 100 parts of a flowable.

The herbicidal effects of the compounds of this invention will be explained below according to test examples.

Test Example 1 (Paddy field soil application)

Suitable amounts of water and a chemical fertilizer were added to paddy field soil. This was filled in 130 cm² plastic pots followed by kneading to convert it to a state of paddy field, to which a stock of paddy field rice plant (variety: Koshihikari) composed of a pair of two seedlings that had been grown in advance in a greenhouse to a stage of two leaves were transplanted in the pots in a population of 1 stock/pot. Further, in each pot, there were sown predetermined amounts of seeds of *Echinochloa crus-galli* P. Beauv., *Monochoria vaginalis* Presl., *Lindernia procumbens* Philcox, and *Scirpus hotarui* Ohwi, respectively, and water was filled to a depth of 3 cm. On the next day, wettable powders were prepared using compounds shown in Table 11 below according to Formulation Example 2, and they were diluted with a suitable amount of water so that they contain active ingredients in amounts of 5 kg or 1 kg per 1 ha. They were applied using a pipette. After 21 days from the application with the chemicals, herbicidal effects on each weed and phytotoxicity on paddy field rice plant were judged according the following criteria. Results obtained are shown in Table 11.

| | Evaluation Criteria (11 Ranks) | |
|---|---|---|
| | Herbicidal Effect | Phototoxicity to Crops |
| | Ratio of Killed Weeds | Ratio of Injured Crops |
| Score | Compared to Control (%) | Compared to Control (%) |
| 0 | 0 | |
| 1 | Above 0 to 10 | Above 0 to 10 |
| 2 | Above 10 to 20 | Above 10 to 20 |
| 3 | Above 20 to 30 | Above 20 to 30 |
| 4 | Above 30 to 40 | Above 30 to 40 |
| 5 | Above 40 to 50 | Above 40 to 50 |
| 6 | Above 50 to 60 | Above 50 to 60 |
| 7 | Above 60 to 70 | Above 60 to 70 |
| 8 | Above 70 to 80 | Above 70 to 80 |
| 9 | Above 80 to 90 | Above 80 to 90 |
| 10 | Above 90 to 100 | Above 90 to 100 |
| | (Withered) | (Withered) |

In the tables 11–18, abbriviations of weeds are as follows.

Weed A: *Echinochloa grus-galli* P. Beauv.
Weed B: *Monochoria Vaginalis* Presl.
Weed C: *Lindernia procumbens* Philcox.
Weed D: *Scirpus hotarui* Ohwi.
Weed E: *Cyperus serotinus* Rott.
Weed F: *Digitaria adscendens* Henr.
Weed G: *Setaria viridis* Beauv.

TABLE 11

| Compound No. | Dose of Active Ingredient g ai/ha | Herbicidal Effect | | | | Phototoxicity Paddy Field Rice Plant |
|---|---|---|---|---|---|---|
| | | Weed A | Weed B | Weed C | Weed D | |
| 5 | 1000 | 10 | 10 | 10 | 10 | 0 |
| | 5000 | 10 | 10 | 10 | 10 | 0 |
| 6 | 1000 | 8 | 9 | 10 | 10 | 0 |
| | 5000 | 10 | 10 | 10 | 10 | 0 |
| 45 | 1000 | 9 | 10 | 10 | 10 | 0 |
| | 5000 | 10 | 10 | 10 | 10 | 0 |
| 63 | 1000 | 9 | 9 | 9 | 9 | 0 |
| | 5000 | 10 | 10 | 10 | 10 | 0 |
| 73 | 1000 | 10 | 10 | 10 | 10 | 0 |
| | 5000 | 10 | 10 | 10 | 10 | 0 |
| 77 | 1000 | 10 | 9 | 10 | 9 | 0 |
| | 5000 | 10 | 10 | 10 | 10 | 0 |
| 78 | 1000 | 10 | 10 | 10 | 10 | 0 |
| | 5000 | 10 | 10 | 10 | 10 | 0 |
| 79 | 1000 | 10 | 10 | 10 | 10 | 0 |
| | 5000 | 10 | 10 | 10 | 10 | 0 |
| 104 | 1000 | 10 | 10 | 10 | 10 | 0 |
| | 5000 | 10 | 10 | 10 | 10 | 0 |
| 135 | 1000 | 10 | 9 | 10 | 10 | 0 |
| | 5000 | 10 | 10 | 10 | 10 | 0 |
| 162 | 1000 | 9 | 9 | 10 | 10 | 0 |
| | 5000 | 10 | 10 | 10 | 10 | 0 |
| 187 | 1000 | 10 | 9 | 10 | 10 | 0 |
| | 5000 | 10 | 10 | 10 | 10 | 0 |
| 217 | 1000 | 10 | 10 | 10 | 10 | 0 |
| | 5000 | 10 | 10 | 10 | 10 | 0 |
| 248 | 1000 | 10 | 10 | 10 | 10 | 0 |
| | 5000 | 10 | 10 | 10 | 10 | 0 |
| 274 | 1000 | 10 | 9 | 10 | 10 | 0 |
| | 5000 | 10 | 10 | 10 | 10 | 0 |
| 283 | 1000 | 9 | 9 | 9 | 9 | 0 |
| | 5000 | 10 | 10 | 10 | 10 | 0 |
| 323 | 1000 | 10 | 9 | 10 | 10 | 0 |
| | 5000 | 10 | 10 | 10 | 10 | 0 |
| 360 | 1000 | 10 | 10 | 10 | 10 | 0 |
| | 5000 | 10 | 10 | 10 | 10 | 0 |
| 363 | 1000 | 10 | 9 | 10 | 10 | 0 |
| | 5000 | 10 | 10 | 10 | 10 | 0 |
| 374 | 1000 | 10 | 10 | 10 | 10 | 0 |
| | 5000 | 10 | 10 | 10 | 10 | 0 |
| 376 | 1000 | 10 | 10 | 10 | 10 | 0 |
| | 5000 | 10 | 10 | 10 | 10 | 0 |
| 388 | 1000 | 10 | 10 | 10 | 10 | 0 |
| | 5000 | 10 | 10 | 10 | 10 | 0 |
| 392 | 1000 | 10 | 10 | 10 | 10 | 0 |
| | 5000 | 10 | 10 | 10 | 10 | 0 |
| 403 | 1000 | 10 | 10 | 10 | 10 | 0 |

TABLE 11-continued

| Compound No. | Dose of Active Ingredient g ai/ha | Herbicidal Effect | | | | Phototoxicity Paddy Field Rice Plant |
|---|---|---|---|---|---|---|
| | | Weed A | Weed B | Weed C | Weed D | |
| | 5000 | 10 | 10 | 10 | 10 | 0 |
| 606 | 1000 | 10 | 10 | 10 | 10 | 0 |
| | 5000 | 10 | 10 | 10 | 10 | 0 |
| 801 | 1000 | 10 | 9 | 10 | 10 | 0 |
| | 5000 | 10 | 10 | 10 | 10 | 0 |
| 857 | 1000 | 10 | 9 | 10 | 10 | 0 |
| | 5000 | 10 | 10 | 10 | 10 | 0 |

Test Example 2 (Paddy field foliar application-1)

Suitable amounts of water and a chemical fertilizer were added to paddy field soil. This was filled in 130 cm² plastic pots followed by kneading to convert it to a state of paddy field, to which a stock of paddy field rice plant (variety: Koshihikari) composed of a pair of two seedlings that had been grown in advance in a greenhouse to a stage of two leaves were transplanted in the pots in a population of 1 stocks/pot. Further, in each pot, there were sown predetermined amounts of seeds of *Echinochloa crus-galli* P. Beauv., *Monochoria vaginalis* Presl., *Lindernia procumbens* Philcox, and *Scirpus hotarui* Ohwi, respectively, and water was filled to a depth of 3 cm. After having grown the plants in a greenhouse until Echinochloa crus-galli P. Beauv. reached a stage of 1.5 leaves, wettable powders were prepared using compounds shown in Table 12 below according to Formulation Example 2, and diluted with a suitable amount of water so that they contain active ingredients in amounts of 5 kg or 1 kg per 1 ha, and then drop-wise applied using a pipette. After 21 days from the application with the chemicals, herbicidal effects on each weed and phytotoxicity on paddy field rice plant were judged according to the criteria in Test Example 1. Results obtained are shown in Table 12.

TABLE 11

| Compound No. | Dose of Active Ingredient g ai/ha | Herbicidal Effect | | | | Phototoxicity Paddy Field Rice Plant |
|---|---|---|---|---|---|---|
| | | Weed A | Weed B | Weed C | Weed D | |
| 5 | 1000 | 10 | 9 | 9 | 6 | 0 |
| | 5000 | 10 | 10 | 10 | 10 | 0 |
| 45 | 1000 | 9 | 8 | 9 | 6 | 0 |
| | 5000 | 10 | 10 | 10 | 10 | 0 |
| 73 | 1000 | 10 | 10 | 10 | 10 | 0 |
| | 5000 | 10 | 10 | 10 | 10 | 0 |
| 77 | 1000 | 10 | 8 | 9 | 6 | 0 |
| | 5000 | 10 | 10 | 10 | 10 | 0 |
| 78 | 1000 | 10 | 9 | 9 | 6 | 0 |
| | 5000 | 10 | 10 | 10 | 10 | 0 |
| 79 | 1000 | 8 | 7 | 9 | 6 | 0 |
| | 5000 | 10 | 10 | 10 | 10 | 0 |
| 104 | 1000 | 10 | 9 | 10 | 8 | 0 |
| | 5000 | 10 | 10 | 10 | 10 | 0 |
| 135 | 1000 | 10 | 8 | 9 | 6 | 0 |
| | 5000 | 10 | 10 | 10 | 10 | 0 |
| 187 | 1000 | 10 | 9 | 9 | 7 | 0 |
| | 5000 | 10 | 10 | 10 | 10 | 0 |
| 217 | 1000 | 10 | 9 | 9 | 8 | 0 |
| | 5000 | 10 | 10 | 10 | 10 | 0 |
| 248 | 1000 | 10 | 7 | 10 | 10 | 0 |
| | 5000 | 10 | 10 | 10 | 10 | 0 |
| 274 | 1000 | 9 | 8 | 10 | 6 | 0 |
| | 5000 | 10 | 10 | 10 | 10 | 0 |
| 323 | 1000 | 10 | 8 | 9 | 7 | 0 |
| | 5000 | 10 | 10 | 10 | 10 | 0 |
| 360 | 1000 | 10 | 10 | 10 | 9 | 0 |
| | 5000 | 10 | 10 | 10 | 10 | 0 |
| 363 | 1000 | 10 | 9 | 9 | 7 | 0 |
| | 5000 | 10 | 10 | 10 | 10 | 0 |
| 374 | 1000 | 10 | 10 | 10 | 10 | 0 |
| | 5000 | 10 | 10 | 10 | 10 | 0 |
| 376 | 1000 | 10 | 10 | 10 | 10 | 0 |
| | 5000 | 10 | 10 | 10 | 10 | 0 |
| 388 | 1000 | 10 | 9 | 9 | 6 | 0 |
| | 5000 | 10 | 10 | 10 | 10 | 0 |
| 392 | 1000 | 10 | 10 | 10 | 10 | 0 |
| | 5000 | 10 | 10 | 10 | 10 | 0 |
| 403 | 1000 | 10 | 10 | 10 | 9 | 0 |
| | 5000 | 10 | 10 | 10 | 10 | 0 |
| 606 | 1000 | 10 | 9 | 10 | 9 | 0 |
| | 5000 | 10 | 10 | 10 | 10 | 0 |
| 801 | 1000 | 10 | 9 | 10 | 9 | 0 |
| | 5000 | 10 | 10 | 10 | 10 | 0 |
| 857 | 1000 | 10 | 9 | 10 | 9 | 0 |
| | 5000 | 10 | 10 | 10 | 10 | 0 |

Test Example 3 (Paddy field foliar application-2)

Suitable amounts of water and a chemical fertilizer were added to paddy field soil. This was filled in 310 cm$^2$ plastic pots followed by kneading to convert it to a state of paddy field, to which a stock of paddy field rice plant (variety: Koshihikari) composed of a pair of two seedlings that had been grown in advance in a greenhouse to a stage of two leaves were transplanted in the pots in a population of 2 stocks/pot. Further, in each pot, there were sown or transplanted predetermined amounts of seeds or bulbs of *Echinochloa crus-galli* P. Beauv., *Monochoria vaginalis* Presl., *Lindernia procumbens* Philcox, and *Cyperus serotinus* Rottb., respectively, and each pot was flushed to a depth of 3 cm. After having grown the plants in a greenhouse until *Echinochloa crus-galli* P. Beauv. reached a stage of 1.5 to 2 leaves, wettable powders were prepared using compounds shown in Table 13 below according to Formulation Example 2, and diluted with a suitable amount of water so that they contain active ingredients in amounts of 150 g, 300 g, 600 g, and 1,200 g, respectively, per 1 ha, and then drop-wise applied using a pipette. After 21 days from the application with the chemicals, herbicidal effects on paddy field rice plant were judged according to the criteria in Test Example 1. Results obtained are shown in Table 13.

Test Example 4 (upland soil application)

Upland soil was filled in 130 cm$^2$ plastic pots, in which there were sown predetermined amounts of seeds of *Echinochloa crus-galli* P. Beauv., *Digitaria adscendens* Henr., and *Setaria viridis* Beauv., respectively, and soil was placed thereon to a thickness of 1 cm. On the next day after the sowing, wettable powders were prepared using compounds shown in Table 14 below according to Formulation Example 2, and they were diluted with a suitable amount of water so that they contain active ingredients in amounts of 5 kg or 1 kg per 1 ha. They were sprayed uniformly on the surface of the soil. After 21 days from the application with the chemicals, herbicidal effects on each weed and phytotoxicity on paddy field rice plant were judged according to the criteria in Test Example 1. Results obtained are shown in Table 14.

TABLE 14

| Compound No. | Dose of Active Ingredient g ai/ha | Herbicidal Effect | | |
|---|---|---|---|---|
| | | Weed A | Weed F | Weed G |
| 73 | 1000 | 10 | 10 | 10 |
| | 5000 | 10 | 10 | 10 |
| 77 | 1000 | 10 | 10 | 10 |
| | 5000 | 10 | 10 | 10 |
| 104 | 1000 | 10 | 10 | 10 |
| | 5000 | 10 | 10 | 10 |
| 135 | 1000 | 10 | 10 | 10 |
| | 5000 | 9 | 10 | 9 |

TABLE 13

| Compound No. | Dose of Active Ingredient g ai/ha | Herbicidal Effect | | | | Phototoxicity Paddy Field Rice Plant |
|---|---|---|---|---|---|---|
| | | Weed A | Weed B | Weed C | Weed E | |
| 73 | 150 | 10 | 10 | 10 | 10 | 0 |
| | 300 | 10 | 10 | 10 | 10 | 0 |
| | 600 | 10 | 10 | 10 | 10 | 0 |
| | 1200 | 10 | 10 | 10 | 10 | 0 |
| 248 | 150 | 10 | 10 | 10 | 10 | 0 |
| | 300 | 10 | 10 | 10 | 10 | 0 |
| | 600 | 10 | 10 | 10 | 10 | 0 |
| | 1200 | 10 | 10 | 10 | 10 | 0 |
| 321 | 150 | 10 | 10 | 9 | 9 | 0 |
| | 300 | 10 | 10 | 10 | 10 | 0 |
| | 600 | 10 | 10 | 10 | 10 | 0 |
| | 1200 | 10 | 10 | 10 | 10 | 0 |
| 360 | 150 | 10 | 9 | 7 | 7 | 0 |
| | 300 | 10 | 9 | 9 | 9 | 0 |
| | 600 | 10 | 10 | 9 | 10 | 0 |
| | 1200 | 10 | 10 | 10 | 10 | 0 |
| 374 | 150 | 10 | 10 | 9 | 9 | 0 |
| | 300 | 10 | 10 | 10 | 9 | 0 |
| | 600 | 10 | 10 | 10 | 10 | 0 |
| | 1200 | 10 | 10 | 10 | 10 | 0 |
| 376 | 150 | 10 | 10 | 9 | 9 | 0 |
| | 300 | 10 | 10 | 10 | 10 | 0 |
| | 600 | 10 | 10 | 10 | 10 | 0 |
| | 1200 | 10 | 10 | 10 | 10 | 0 |
| 392 | 150 | 10 | 10 | 10 | 10 | 0 |
| | 300 | 10 | 10 | 10 | 10 | 0 |
| | 600 | 10 | 10 | 10 | 10 | 0 |
| | 1200 | 10 | 10 | 10 | 10 | 0 |
| 403 | 150 | 10 | 9 | 9 | 9 | 0 |
| | 300 | 10 | 10 | 10 | 9 | 0 |
| | 600 | 10 | 10 | 10 | 10 | 0 |
| | 1200 | 10 | 10 | 10 | 10 | 0 |
| 406 | 150 | 10 | 10 | 10 | 9 | 0 |
| | 300 | 10 | 10 | 10 | 10 | 0 |
| | 600 | 10 | 10 | 10 | 10 | 0 |
| | 1200 | 10 | 10 | 10 | 10 | 0 |
| 606 | 150 | 10 | 10 | 10 | 9 | 0 |
| | 300 | 10 | 10 | 10 | 10 | 0 |
| | 600 | 10 | 10 | 10 | 10 | 0 |
| | 1200 | 10 | 10 | 10 | 10 | 0 |

TABLE 14-continued

| Compound No. | Dose of Active Ingredient g ai/ha | Herbicidal Effect | | |
|---|---|---|---|---|
| | | Weed A | Weed F | Weed G |
| 187 | 1000 | 10 | 10 | 10 |
| | 5000 | 10 | 10 | 10 |
| 217 | 1000 | 10 | 10 | 10 |
| | 5000 | 10 | 10 | 10 |
| 248 | 1000 | 10 | 10 | 10 |
| | 5000 | 10 | 10 | 10 |
| 274 | 1000 | 10 | 10 | 10 |
| | 5000 | 10 | 10 | 10 |
| 323 | 1000 | 10 | 10 | 10 |
| | 5000 | 10 | 10 | 10 |
| 359 | 1000 | 10 | 10 | 10 |
| | 5000 | 10 | 10 | 10 |
| 363 | 1000 | 10 | 10 | 10 |
| | 5000 | 10 | 10 | 10 |
| 374 | 1000 | 10 | 10 | 10 |
| | 5000 | 10 | 10 | 10 |
| 392 | 1000 | 10 | 10 | 10 |
| | 5000 | 10 | 10 | 10 |
| 606 | 1000 | 10 | 10 | 10 |
| | 5000 | 10 | 10 | 10 |

Example 5 (Upland foliar application)

Upland soil was filled in 130 cm plastic pots, in which there were sown predetermined amounts of seeds of *Echinochloa crus-galli* P. Beauv., *Digitaria adscendens* Henr., and *Setaria viridis* Beauv., respectively, and soil was placed thereon to a thickness of 1 cm. After the sowing, the pots were placed in a glass greenhouse and the plants were grown until they reached a stage of 2–4 leaves. Thereafter, wettable powders were prepared using compounds shown in Table 15 below according to Formulation Example 2, and they were diluted with a suitable amount of water so that they contain active ingredients in amounts of 5 kg or 1 kg per 1 ha. They were sprayed uniformly on the surface of the soil. After 21 days from the application with the chemicals, herbicidal effects on each weed and phytotoxicity on paddy field rice plant were judged according to the criteria in Test Example 1. Results obtained are shown in Table 15.

TABLE 15

| Compound No. | Dose of Active Ingredient g ai/ha | Herbicidal Effect | | |
|---|---|---|---|---|
| | | Weed A | Weed F | Weed G |
| 73 | 1000 | 10 | 10 | 10 |
| | 5000 | 10 | 10 | 10 |
| 104 | 1000 | 10 | 10 | 9 |
| | 5000 | 10 | 10 | 10 |
| 248 | 1000 | 10 | 10 | 10 |
| | 5000 | 10 | 10 | 10 |
| 274 | 1000 | 10 | 10 | 9 |
| | 5000 | 10 | 10 | 10 |
| 360 | 1000 | 10 | 10 | 10 |
| | 5000 | 10 | 10 | 10 |
| 374 | 1000 | 10 | 10 | 10 |
| | 5000 | 10 | 10 | 10 |
| 392 | 1000 | 10 | 10 | 10 |
| | 5000 | 10 | 10 | 10 |
| 606 | 1000 | 3 | 4 | 3 |
| | 5000 | 10 | 10 | 10 |

Test Example 6 (Water seeded foliar application)

A chemical fertilizer was put in each of 200 cm² Wagner pots, which were then filled with coarse clod paddy field soil. Then, water was added thereto until the clods sank therein completely, and rice plant seeds (variety: Koshihikari) germinated in advance were sown uniformly in a population amounting to 120 kg/ha. Simultaneously, a predetermined amount of seeds of *Echinochloa crus-galli* P. Beauv. were sown and grown in a greenhouse until it reached stages of 1 leaf, 2 leaves and 3 leaves. In these stages, the leaf ages of the rice plant were 0.5 leaf, 1.5 leaves and 2.5 leaves, respectively. When the weed reached each leaf age, wettable powders were prepared using compounds shown in Table 16 below according to Formulation Example 2, and diluted with a suitable amount of water so that they contain active ingredients in amounts of 50 g, 75 g, 100 g, 150 g and 200 g, per 1 ha, and then drop-wise applied using a pipette. After 30 days from the application with the chemicals, herbicidal effects on the weed and phytotoxicity on the paddy field rice plant were judged according to the criteria in Test Example 1. Results obtained are shown in Table 16.

TABLE 16

| Compound No. | Dose of Active Ingredient a ai/ha | Herbicidal Effect Leaf Age in Leaf Number of Weed A | | | Phytotoxicity Leaf Age in Leaf Number of Paddy Field Rice Plant | | |
|---|---|---|---|---|---|---|---|
| | | 1.0 | 2.0 | 3.0 | 0.5 | 1.5 | 2.5 |
| 73 | 50 | 10 | 10 | 10 | 0 | 0 | 0 |
| | 75 | 10 | 10 | 10 | 0 | 0 | 0 |
| | 100 | 10 | 10 | 10 | 1 | 0 | 0 |
| | 150 | 10 | 10 | 10 | 1 | 0 | 0 |
| | 200 | 10 | 10 | 10 | 3 | 2 | 1 |
| 248 | 50 | 10 | 10 | 10 | 0 | 0 | 0 |
| | 75 | 10 | 10 | 10 | 0 | 0 | 0 |
| | 100 | 10 | 10 | 10 | 0 | 0 | 0 |
| | 150 | 10 | 10 | 10 | 1 | 0 | 0 |
| | 200 | 10 | 10 | 10 | 1 | 1 | 1 |
| 606 | 50 | 10 | 10 | 9 | 0 | 0 | 0 |
| | 75 | 10 | 10 | 10 | 0 | 0 | 0 |
| | 100 | 10 | 10 | 10 | 0 | 0 | 0 |
| | 150 | 10 | 10 | 10 | 1 | 0 | 0 |
| | 200 | 10 | 10 | 10 | 1 | 1 | 1 |

Test Example 7 (Dry-seeded foliar application)

A chemical fertilizer was put in each of 200 cm² plastic pots, which were then filled with coarse clod farmland soil. Then, rice plant seeds amounting to 120 kg/ha and a predetermined amount of seeds of *Echinochloa crus-galli* P. Beauv. were sown in a depth of 2 cm, and grown in a greenhouse. During the growth, each pot was flushed for 24 hours immediately after the sowing, at a stage of 1 leaf, and at a stage of 2 leaves. After completion of the flushing at the stage of 2 leaves of the rice plant, water was added to a flushing depth of 5 cm. Incidentally, the leaf age in leaf number of *Echinochloa crus-galli* P. Beauv. was 3 leaves. Then, wettable powders were prepared using compounds shown in Table 17 below according to Formulation Example 2, and diluted with a suitable amount of water so that they contain active ingredients in amounts of 50 g, 100 g, 150 g and 200 g, per 1 ha, and then drop-wise applied using a pipette. After 30 days from the application with the chemicals, herbicidal effects on the weed and phytotoxicity on the rice plant were judged according to the criteria in Text Example 1. Results obtained are shown in Table 17.

TABLE 17

| Compound No. | Dose of Active Ingredient g ai/ha | Herbicidal Effect | Phytotoxicity |
|---|---|---|---|
| 73 | 50 | 10 | 0 |
| | 100 | 10 | 0 |

TABLE 17-continued

| Compound No. | Dose of Active Ingredient g ai/ha | Herbicidal Effect | Phyto-toxicity |
|---|---|---|---|
|  | 150 | 10 | 0 |
|  | 200 | 10 | 0 |
| 248 | 50 | 10 | 0 |
|  | 100 | 10 | 0 |
|  | 150 | 10 | 0 |
|  | 200 | 10 | 0 |
| 606 | 50 | 9 | 0 |
|  | 100 | 10 | 0 |
|  | 150 | 10 | 0 |
|  | 200 | 10 | 0 |

Test Example 8 (Upland soil application-2)

Farmland soil was filled in 900 cm² plastic pots, in which there were sown predetermined amounts of seeds of *Echinochloa crus-galli* P. Beauv., *Digitaria ascendens* Henr., and *Setaria viridis* Beauv., respectively, and soil was placed thereon to a thickness of 2 cm. On the next day after the sowing, wettable powders were prepared using compounds shown in Table 18 below according to Formulation Example 2, and they were diluted with a suitable amount of water so that they contain active ingredients in amounts of 50 g, 100 g, 200 g, 400 g, 800 g, or 1,600 g, per 1 ha. They were sprayed uniformly on the surface of the soil. After 30 days from the application with the chemicals, herbicidal effects on each weed and phytotoxicity on paddy field rice plant were judged according to the criteria in Test Example 1. Results obtained are shown in Table 18.

TABLE 18

| Compound No. | Dose of Active Ingredient g ai/ha | Herbicidal Effect | | |
|---|---|---|---|---|
|  |  | Weed A | Weed F | Weed G |
| 73 | 50 | 10 | 10 | 10 |
|  | 100 | 10 | 10 | 10 |
|  | 200 | 10 | 10 | 10 |
|  | 400 | 10 | 10 | 10 |
|  | 800 | 10 | 10 | 10 |
|  | 1600 | 10 | 10 | 10 |
| 248 | 50 | 9 | 10 | 10 |
|  | 100 | 10 | 10 | 10 |
|  | 200 | 10 | 10 | 10 |
|  | 400 | 10 | 10 | 10 |
|  | 800 | 10 | 10 | 10 |
|  | 1600 | 10 | 10 | 10 |
| 359 | 50 | 10 | 10 | 10 |
|  | 100 | 10 | 10 | 10 |
|  | 200 | 10 | 10 | 10 |
|  | 400 | 10 | 10 | 10 |
|  | 800 | 10 | 10 | 10 |
|  | 1600 | 10 | 10 | 10 |
| 606 | 50 | 9 | 10 | 10 |
|  | 100 | 10 | 10 | 10 |
|  | 200 | 10 | 10 | 10 |
|  | 400 | 10 | 10 | 10 |
|  | 800 | 10 | 10 | 10 |
|  | 1600 | 10 | 10 | 10 |

Industrial Applicability

As described above, the compounds of this invention have broad herbicidal spectra and potent herbicidal activities and in addition high safety to useful crops, so that they are useful as herbicides.

We claim:

1. A 1,3-oxazin-4-one derivative of the formula (I)

$$
\begin{array}{c}
\text{(I)}
\end{array}
$$

wherein $R^1$ is a lower alkyl group, a lower alkenyl group, an aryl group which may be substituted, or an aralkyl group which may be substituted;

$R^2$ is a hydrogen atom or a lower alkyl group, $R^3$ is a lower alkyl group, an aryl group which may be substituted, or an aralkyl group which may be substituted; and $R^4$ and $R^5$, independently, each is a lower alkyl group, or $R^4$ and $R^5$ taken together with the carbon atom to which they are bonded, combine to form a 3- to 8-membered carbocyclic group which may possess a lower alkyl group as a ring substituent.

2. A compound according to claim 1, wherein $R^1$ is a branched chain lower alkyl group or a phenyl group which may be substituted with one substituent selected from the group consisting of a halogen atom and a lower alkyl group;

$R^2$ is a methyl group or an ethyl group;

$R^3$ is an aryl group which may be substituted with 1 to substituents selected from the group consisting of a halogen atom, a lower alkyl group, a lower haloalkyl group and a lower haloalkoxy group; and $R^4$ and $R^9$ each is a methyl group.

3. A compound according to claim 1 of the formula $$
\begin{array}{c}
\text{(I-1)}
\end{array}
$$

wherein $R^{21}$ is a methyl group or an ethyl group;

X is a halogen atom or a lower alkyl group;

Y is a halogen atom, a lower haloalkyl group or a lower haloalkoxy group;

m is 0, 1, 2 or 3; and n is 0 or 1.

4. A compound of claim 3 which is 6-methyl-3-[1-methyl-1(3,5-dichlorophenyl) ethyl]-5-phenyl-2,3-dihydro-4H-1,3-oxazine-4-one.

5. A method of producing a 1,3-oxazin-4-one derivative of formula (I) as described in claim 1, comprising the step of:

reacting a compound of the formula $$
\begin{array}{c}
\text{(II)}
\end{array}
$$

wherein $R^1$ and $R^2$ are as defined in claim 1, with a compound of the formula $$
\begin{array}{c}
\text{(III)}
\end{array}
$$

wherein $R^3$, $R^4$ and $R^5$ are as defined in claim 1.

6. A herbicide comprising as an active ingredient a 1,3-oxaxzin-4-one derivative as defined in claim 1.

7. A herbicidal composition comprising an effective amount of a 1,3-oxazin-4-one derivative as defined in claim 1, and an agriculturally or horticulturally acceptable carrier or diluent.

8. A method of controlling weeds, comprising the step of:
   applying an effective amount of a 1,3-oxazin-4-one derivative as defined in claim 1 to a place to be protected.

* * * * *